(12) United States Patent
Li

(10) Patent No.: US 9,079,876 B2
(45) Date of Patent: Jul. 14, 2015

(54) IMIDAZOLE DERIVATIVES AND PREPARATION METHOD AND USE THEREOF

(75) Inventor: Jin Li, Beijing (CN)

(73) Assignee: Beijing Orbiepharm Co., Ltd., Haidian, Beijing (CN)

(*) Notice: Subject to any disclaimer, the term of this patent is extended or adjusted under 35 U.S.C. 154(b) by 0 days.

(21) Appl. No.: 13/882,855

(22) PCT Filed: Oct. 14, 2011

(86) PCT No.: PCT/CN2011/080820
§ 371 (c)(1),
(2), (4) Date: May 1, 2013

(87) PCT Pub. No.: WO2012/059001
PCT Pub. Date: May 10, 2012

(65) Prior Publication Data
US 2013/0225638 A1 Aug. 29, 2013
US 2014/0045901 A2 Feb. 13, 2014

(30) Foreign Application Priority Data

Nov. 2, 2010 (CN) .......................... 2010 1 0527144
Jun. 15, 2011 (CN) .......................... 2011 1 0160496

(51) Int. Cl.
*C07D 401/04* (2006.01)
*C07D 401/14* (2006.01)
*A61K 31/4439* (2006.01)

(52) U.S. Cl.
CPC .......... *C07D 401/04* (2013.01); *A61K 31/4439* (2013.01); *C07D 401/14* (2013.01)

(58) Field of Classification Search
CPC . C07D 401/04; C07D 401/14; A61K 31/4439
USPC ........................................ 514/341; 546/274.1
See application file for complete search history.

(56) References Cited

U.S. PATENT DOCUMENTS 6,838,476 B1 * 1/2005 Almansa et al. ............... 514/399
7,019,144 B2 * 3/2006 Cho et al. .................... 546/272.4
7,135,572 B2 * 11/2006 Cho et al. .................... 546/272.4

FOREIGN PATENT DOCUMENTS

| EP | 1122243 A1 | 8/2001 |
| EP | 1270559 A1 | 1/2003 |
| JP | 2002527508 A | 8/2002 |
| JP | 2003528086 A | 9/2003 |
| JP | 2005518396 A | 6/2005 |
| JP | 2006512385 A | 4/2006 |
| WO | 03055875 A1 | 7/2003 |
| WO | 2004024691 A1 | 3/2004 |
| WO | 2004058778 A1 | 7/2004 |
| WO | 2004099130 A2 | 11/2004 |

OTHER PUBLICATIONS

Lablanche; Eur. J. Med. Chem., 1976, 11, 139-143.*
Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Almansa; J. Med. Chem. 2003, 46, 3463-3475.*
Soliva; J. Med. Chem. 2003, 46, 1372-1382.*
Li; Bioorganic & Medicinal Chemistry Letters, 14 (2004) 95-98.*
Sakya; Bioorganic and Medicinal Chemistry Letters, 2008, 18, 1042-1045.*
Gierse; Veterinary therapeutics, 2002, 3, 270-280.*
English Translation of International Search Report and Written Opinion for Corresponding International Application No. PCT/CN2011/080820 (mailed Jan. 19, 2012).
Wang et al., "Study of Quantitative Structure-Activity Relationships of 1,5-Diarylimidazole COX-2 Inhibitors," Journal of Beijing University of Chemical Technology 33(2):92-96 (2006) (English abstract only).
Zhang et al., "A QSAR Study of 1,2-diarylimidazole Cyclooxygenase-2 Inhibitors," Computers and Applied Chemistry 25(3):293-297 (2008) (English abstract only).
International Search Report (Chinese) for corresponding International Application No. PCT/CN2011/080820, (mailed Jan. 19, 2012).
Supplementary European Search Report for European Application No. 11837527.8 (Mar. 13, 2014).
Wermuth, C.G. (ed.), "The Practice of Medicinal Chemistry," vol. 1, Technomics, Inc., pp. 235-271 (Aug. 15, 1998) (English translation of section II(D) on pp. 243-244).
Notice of Reasons for Rejection and English Translation for JP Patent Application No. 2013-535260 (dated Oct. 7, 2014).

* cited by examiner

*Primary Examiner* — John Mabry
*Assistant Examiner* — Daniel Carcanague
(74) *Attorney, Agent, or Firm* — LeClairRyan, a Professional Corporation

(57) ABSTRACT

Disclosed are imidazole derivatives as represented by formula (I), and preparation method and use thereof. The compounds can inhibit cyclooxygenase and treat diseases mediated by cyclooxygenase.

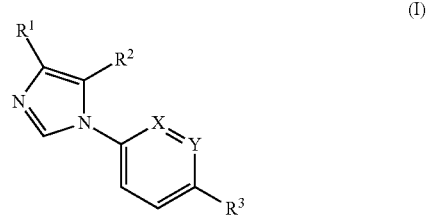

(I)

14 Claims, No Drawings

IMIDAZOLE DERIVATIVES AND PREPARATION METHOD AND USE THEREOF

This application is a national stage application under 35 U.S.C. §371 of PCT Application No. PCT/CN2011/080820, filed Oct. 14, 2011, which claims the benefit of China Patent Application No. CN 201110160496.5, filed Jun. 15, 2011, and China Patent Application No. CN 201010527144.4, filed Nov. 2, 2010, both of which are hereby incorporated by reference in their entirety.

FIELD OF THE INVENTION

The present disclosure relates to the use of a novel class of imidazole derivatives and pharmaceutical compositions thereof in treating diseases associated with cyclooxygenase. The compounds of the present disclosure can inhibit cyclooxygenase, and interfere with the in vivo biotransformation from arachidonic acid to prostaglandin. Therefore, they can be used in treating and alleviating inflammation and various diseases caused by inflammation in human and animals, for example, arthritis, neurodegenerative disease, depression, schizophrenia and mammalian colon cancer, as well as human colon cancer.

BACKGROUND

Metabolites of arachidonic acids are involved in the pathogenesis of many acute and chronic inflammatory conditions. The class of lipoid metabolites of arachidonic acid is generated through a series of enzyme actions. The most important enzyme in terms of treatment is prostaglandin G/H synthase, i.e. cyclooxygenase (COX), which catalyzes the production of various angiotensin and inflammatory substances, such as prostaglandin ($PGE_2$, $PGD_2$, $PGF_2$), prostacyclin ($PGI_2$), and thromboxane ($TXA_2$), etc.

Non-steroidal anti-inflammatory drugs (NSAIDs) have been widely used for treating pain and arthritis due to their significant anti-inflammatory and analgesic effects. NSAIDs work mainly by inhibiting cyclooxygenase (COX), i.e. prostaglandin G/H synthase (PGHs), thereby inhibiting the metabolism of arachidonic acid into prostaglandins. Prostaglandin, especially prostaglandin $PGE_2$, is a major mediator contributing to pain, fever and the other symptoms associated with inflammation, and is the major arachidonic acid detected when inflammation occurs. Inhibition of prostaglandin biosynthesis has been proved to be an important target of anti-inflammatory drugs. However, therapeutic use of traditional non-steroidal anti-inflammatory drugs is significantly limited due to their side effects of life-threatening ulcers and renal toxicity. Corticosteroid drugs can serve as alternatives for NSAIDs, however, their long-term use will produce serious side effects as well.

In early 1990s, cyclooxygenase was found existing in two enzyme types, COX-1 and COX-2. COX-1 is present in many normal tissues such as stomach, kidney and platelets. Gastrointestinal and renal side effects caused by NSAIDs are resulted from COX-1 inhibition. COX-2 is inducible. When induced by a series of inflammatory factors or cytokines, COX-2 can be expressed in large quantity in many tissues, such as macrophages, bone cells, fibroblasts and endothelial cells.

The discovery of COX-2 makes synthesis of selective COX-2 inhibitors possible. The highly selective COX-2 inhibitors greatly reduced COX-1 inhibition, thereby reducing the ulcer toxicity, and improving the gastrointestinal tolerability of these drugs. The present disclosure discloses a novel class of selective COX-2 inhibitors.

SUMMARY OF THE INVENTION

The present disclosure relates to a compound of formula (I),

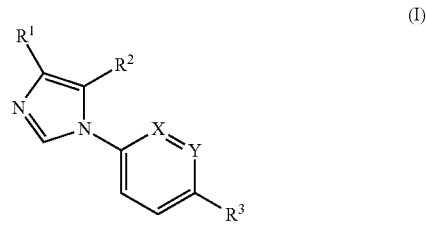

wherein:
when X=N, Y=C or Y=N, X=C atom;
substituent group $R^1$ represents hydrogen atom, $C_{1-5}$ alkyl, halogen or cyano group;
substituent group $R^2$ represents aryl or heteroaryl substituted independently by one or more groups which can be halogen, $C_{1-8}$ alkyl, $R^4OC_{0-8}$alkyl, $R^4SC_{0-8}$alkyl, cyano group, nitro group, —$NR^4R^6$, —$NR^4SO_2R^5$, —$SOR^5$, —$SO_2R^5$, —$SO_2NR^4R^6$ or —$CONR^4R^6$;
substituent group $R^3$ represents group —$SOR^7$, —$SO_2R^7$ or —$SR^7$;
substituent group $R^4$ represents hydrogen atom, $C_{1-8}$ alkyl, $C_{1-8}$ haloalkyl, aryl $C_{0-8}$ alkyl, wherein the aryl is optionally substituted by one or more groups which can be $C_{1-8}$ alkyl, halogen, $C_{1-8}$ haloalkyl, cyano group or nitro group;
substituent group $R^5$ represents $C_{1-8}$ alkyl or $C_{1-8}$ haloalkyl;
substituent group $R^6$ represents hydrogen atom, $C_{1-8}$ alkyl or aryl $C_{0-8}$ alkyl, wherein the aryl is optionally substituted by one or more groups which can be $C_{1-8}$ alkyl, halogen, $C_{1-8}$ haloalkyl, cyano group or nitro group; and
substituent group $R^7$ represents —$NH_2$, $C_{1-8}$ alkyl or $C_{1-8}$ haloalkyl.

In an hydrocarbon portion as provided herein, the number of carbon atoms is defined with a prefix of the minimum number and a prefix of the maximum number of carbon atoms, for example, an alkyl with the prefix of $C_{a-b}$ represents an alkyl containing a to b carbon atoms. Thus, $C_{1-8}$ alkyl refers to an alkyl containing 1-8 carbon atoms.

An "alkoxy" refers to a straight or branched, monovalent, saturated carbon aliphatic chain bonding to an oxygen atom, including, but not limited to, such as methoxy, ethoxy, propoxy, butoxy, isobutoxy, tert-butoxy, and the like.

An "alkyl" refers to a straight or branched, monovalent, saturated carbon aliphatic chain, including, but not limited to, such as methyl, ethyl, propyl, isopropyl, butyl, isobutyl, tert-butyl, pentyl, isopentyl, hexyl, and the like.

An "aryl" refers to a cyclic aromatic hydrocarbon, including, but not limited to, such as phenyl, naphthyl, anthryl, phenanthryl, and the like.

A "halogen" refers to a chlorine, bromine, fluorine and iodine atom or group.

A "heteroaryl" refers to a monocyclic or polycyclic aromatic hydrocarbon wherein one or more carbon atoms are substituted by a heteroatom such as nitrogen, oxygen or sulfur. If the heteroaryl contains more than one heteroatom, these substituted heteroatoms can be the same or different.

The heteroaryl includes, but not limited to, such as benzofuranyl, benzothienyl, benzimidazolyl, benzoxazolyl, benzothiazolyl, benzopyranyl, furyl, imidazolyl, indozolyl, indolizinyl, indolyl, isobenzofuranyl, isoindolyl, isoquinolyl, isothiazolyl, isoxazolyl, naphthyridinyl, oxadiazolyl, oxazinyl, oxazolyl, phthalazinyl, pteridinyl, purinyl, pyranyl, pyrazinyl, pyrazolyl, pyridazinyl, pyridine [3,4-b]indolyl, pyridyl, pyrimidyl, pyrrolyl, quinolizinyl, quinolyl, quinoxaline, thiadiazolyl, thiatriazolyl, thiazolyl, thienyl, triazinyl, triazolyl, xanthenyl, and the like.

"Substituted" means that the hydrogen atom in a molecule is replaced by another different atom or molecule. The atom or the molecule replacing the hydrogen atom is referred to as a "substituent group."

An embodiment of the present disclosure encompasses a group of compounds having the structure of formula (I), wherein the compounds are structurally characterized in that:

when X=N, Y=C or Y=N, X=C atom, substituent group $R^1$ represents hydrogen atom, $C_{1-5}$ alkyl, halogen or cyano group;

substituent group $R^2$ represents aryl or heteroaryl substituted independently by one or more groups which can be halogen, $C_{1-8}$ alkyl, $R^4OC_{0-8}$ alkyl, $R^4SC_{0-8}$ alkyl, cyano group, nitro group, —$NR^4R^6$, $NR^4SO_2R^5$, —$SOR^5$, —$SO_2R^5$, —$SO_2NR^4R^6$ or —$CONR^4R^6$;

substituent group $R^3$ represents group —$SOR^7$, —$SO_2R^7$ or —$SR^7$;

substituent group $R^4$ represents hydrogen atom, $C_{1-8}$ alkyl, $C_{1-8}$ haloalkyl, aryl $C_{0-8}$ alkyl, wherein the aryl is optionally substituted by one or more groups which can be $C_{1-8}$ alkyl, halogen, $C_{1-8}$ haloalkyl, cyano group or nitro group;

substituent group $R^5$ represents $C_{1-8}$ alkyl or $C_{1-8}$ haloalkyl;

substituent group $R^6$ represents hydrogen atom, $C_{1-8}$ alkyl or aryl $C_{0-8}$ alkyl, wherein the aryl is optionally substituted by one or more groups which can be $C_{1-8}$ alkyl, halogen, $C_{1-8}$ haloalkyl, cyano group or nitro group;

the aryl is phenyl or naphthyl; the heteroaryl refers to a heteroaryl that can be combined with a benzene ring in parallel, such as pyridine, pyrazine, pyrimidine or pyridazine; and substituent group $R^7$ represents —$NH_2$, $C_{1-8}$ alkyl or $C_{1-8}$ haloalkyl.

Another embodiment of the present disclosure encompasses a group of compounds having the structure of formula (I), wherein the compounds are structurally characterized in that:

when X=N, Y=C or Y=N, X=C atom, substituent group $R^1$ represents hydrogen atom, $C_{1-5}$ alkyl or halogen;

substituent group $R^2$ represents aryl or heteroaryl substituted independently by one or more groups which can be halogen, $C_{1-8}$ alkyl, $R^4OC_{0-8}$ alkyl, $R^4SC_{0-8}$ alkyl, nitro group, —$NR^4R^6$ and —$SOR^5$;

substituent group $R^3$ represents group —$SR^7$ or —$SO_2R^7$;

substituent group $R^4$ represents hydrogen atom, $C_{1-8}$ alkyl or $C_{1-8}$ haloalkyl;

substituent group $R^5$ represents $C_{1-8}$ alkyl or $C_{1-8}$ haloalkyl;

aryl is phenyl, the heteroaryl is pyridine; and substituent group $R^7$ represents —$NH_2$ or $C_{1-8}$ alkyl.

Another embodiment of the present disclosure encompasses a group of compounds having the structure of formula (I), wherein the compounds is structurally characterized in that:

when X=N, Y=C or Y=N, X=C atom, substituent group $R^1$ represents hydrogen atom, $C_{1-3}$ alkyl or halogen;

substituent group $R^2$ represents aryl or heteroaryl independently substituted by one or more groups, wherein the substituted groups can be halogen, $C_{1-5}$ alkyl, $R^4OC_{0-5}$ alkyl, $R^4SC_{0-5}$ alkyl, nitro group, —$NR^4R^6$, or —$SOR^5$;

substituent group $R^3$ represents group —$SR^7$, or —$SO_2R^7$;

substituent group $R^4$ represents hydrogen atom, $C_{1-5}$ alkyl, or $C_{1-5}$ haloalkyl;

substituent group $R^5$ represents $C_{1-5}$ alkyl or $C_{1-5}$ haloalkyl;

substituent group $R^6$ represents hydrogen atom, $C_{1-5}$ alkyl, or aryl $C_{0-5}$ alkyl, wherein the aryl is optionally substituted by one or more groups which can be $C_{1-5}$ alkyl, halogen, $C_{1-5}$ haloalkyl, cyano group or nitro group; and substituent group $R^7$ represents $C_{1-5}$ alkyl.

Another embodiment of the present disclosure encompasses a group of compounds having the structure of formula (I), wherein the compounds are structurally characterized in that:

when X=N, Y=C or Y=N, X=C atom, substituent group $R^1$ represents hydrogen atom, $C_{1-3}$ alkyl, or halogen;

substituent group $R^2$ represents aryl or heteroaryl independently substituted by one or more groups, wherein the substituted groups can be halogen, $C_{1-4}$ alkyl, $R^4OC_{0-4}$ alkyl, $R^4SC_{0-4}$ alkyl, nitro group, —$NR^4R^6$, or —$SOR^5$;

substituent group $R^3$ represents group —$SR^7$ or —$SO_2R^7$;

substituent group $R^4$ represents hydrogen atom, $C_{1-4}$ alkyl, or $C_{1-4}$ haloalkyl;

substituent group $R^5$ represents $C_{1-4}$ alkyl or $C_{1-4}$ haloalkyl;

substituent group $R^6$ represents hydrogen atom, $C_{1-4}$ alkyl, or aryl $C_{0-4}$ alkyl, wherein the aryl is optionally substituted by one or more groups which can be $C_{1-4}$ alkyl, halogen, $C_{1-4}$ haloalkyl, cyano group, or nitro group; and substituent group $R^7$ represents $C_{1-4}$ alkyl.

Another embodiment of the present disclosure encompasses a group of compounds having the structure of formula (I), wherein the compounds are structurally characterized in that:

when X=N, Y=C or Y=N, X=C atom, substituent group $R^1$ represents hydrogen atom, chlorine atom, bromine atom or $C_{1-3}$ alkyl;

substituent group $R^2$ represents aryl or heteroaryl substituted independently by one or more groups which can be halogen, $C_{1-3}$ alkyl, $R^4OC_{0-4}$ alkyl, $R^4SC_{0-4}$ alkyl, nitro group, amino group, or —$SOR^5$;

substituent group $R^3$ represents group —$SR^7$ or —$SO_2R^7$;

substituent group $R^4$ represents $C_{1-4}$ alkyl or, $C_{1-4}$ haloalkyl; and substituent group $R^5$ represents $C_{1-3}$ alkyl.

Another embodiment of the present disclosure encompasses a group of compounds having the structure of formula (I), wherein the compounds are structurally characterized in that:

when X=N, Y=C or Y=N, X=C atom, substituent group $R^1$ represents hydrogen atom, chlorine atom, or methyl;

substituent group $R^2$ represents aryl or heteroaryl independently substituted by one or more groups which can be halogen, $C_{1-3}$ alkyl, $C_{1-3}$alkoxyl, $R^4OC_{0-4}$alkyl, $R^4SC_{0-4}$alkyl, nitro group, amino group, or —$SOR^5$;

substituent group R³ represents group —SR⁷, or —SO₂R⁷;
substituent group R⁴ represents $C_{1-3}$ alkyl or $C_{1-3}$ haloalkyl;
substituent group R⁵ represents $C_{1-3}$ alkyl; and
substituent group R⁷ represents methyl.

In a preferred embodiment of the present disclosure, the compound of formula (I) is selected from:
2-(4-chloro-5-phenyl-1H-imidazol-1-yl)-5-(methylsulfonyl)pyridine,
5-(methylsulfonyl)-2-(5-phenyl-1H-imidazol-1-yl)pyridine,
2-(4-chloro-5-(4-fluorophenyl)-1H-imidazol-1-yl)-5-(methylsulfonyl)pyridine,
2-(5-(4-fluorophenyl)-1H-imidazol-1-yl)-5-(methylsulfonyl)pyridine,
2-(4-chloro-5-p-tolyl-1H-imidazol-1-yl)-5-(methylsulfonyl)pyridine,
5-(methylsulfonyl)-2-(5-p-tolyl-1H-imidazol-1-yl)pyridine,
2-(4-chloro-5-(2,4-dichlorophenyl)-1H-imidazol-1-yl)-5-(methylsulfonyl)pyridine,
2-(5-(2,4-dichlorophenyl)-1H-imidazol-1-yl)-5-(methylsulfonyl)pyridine,
2-(4-chloro-5-(4-methoxyphenyl)-1H-imidazol-1-yl)-5-(methylsulfonyl)pyridine,
2-(5-(4-methoxyphenyl)-1H-imidazol-1-yl)-5-(methylsulfonyl)pyridine,
2-(4-chloro-5-(3-fluoro-4-methoxyphenyl)-1H-imidazol-1-yl)-5-(methylsulfonyl)pyridine,
2-(5-(3-fluoro-4-methoxyphenyl)-1H-imidazol-1-yl)-5-(methylsulfonyl)pyridine,
2-(4-chloro-5-(pyridin-3-yl)-1H-imidazol-1-yl)-5-(methylsulfonyl)pyridine,
5-(4-chloro-5-phenyl-1H-imidazol-1-yl)-2-(methylsulfonyl)pyridine,
2-(methylsulfonyl)-5-(5-phenyl-1H-imidazol-1-yl)pyridine,
5-(4-chloro-5-(4-methoxyphenyl)-1H-imidazol-1-yl)-2-(methylsulfonyl)pyridine,
5-(4-chloro-5-(3-fluoro-4-methoxyphenyl)-1H-imidazol-1-yl)-2-(methylsulfonyl)pyridine,
5-(4-chloro-5-(pyridin-3-yl)-1H-imidazol-1-yl)-2-(methylsulfonyl)pyridine,
5-(4-chloro-5-(4-fluorophenyl)-1H-imidazol-1-yl)-2-(methylsulfonyl)pyridine,
2-(4-chloro-5-(3-chloro-4-methoxyphenyl)-1H-imidazol-1-yl)-5-(methylsulfonyl)pyridine,
2-(4-chloro-5-(3-fluorophenyl)-1H-imidazol-1-yl)-5-(methylsulfonyl)pyridine,
2-(4-chloro-5-(3-fluoro-4-methylphenyl)-1H-imidazol-1-yl)-5-(methylsulfonyl)pyridine,
2-(4-chloro-5-(2-fluorophenyl)-1H-imidazol-1-yl)-5-(methylsulfonyl)pyridine,
2-(5-(2,4-difluorophenyl)-1H-imidazol-1-yl)-5-(methylsulfonyl)pyridine,
2-(5-(2,4-dichlorophenyl)-1H-imidazol-1-yl)-5-(methylsulfonyl)pyridine,
2-(5-(3-fluorophenyl)-1H-imidazol-1-yl)-5-(methylsulfonyl)pyridine,
2-(5-(3-fluoro-4-methylphenyl)-1H-imidazol-1-yl)-5-(methylsulfonyl)pyridine,
2-(5-(2-fluorophenyl)-1H-imidazol-1-yl)-5-(methylsulfonyl)pyridine,
5-(methylsulfonyl)-2-(5-(4-(trifluoromethoxy)phenyl)-1H-imidazol-1-yl)pyridine,
4-methyl-3-(1-(5-(methylsulfonyl)pyridin-2-yl)-1H-imidazol-5-yl)pyridine,
2-(5-(2-fluoro-4-methoxyphenyl)-1H-imidazol-1-yl)-5-(methylsulfonyl)pyridine,
2-(5-(3-chloro-4-methyl)-1H-imidazol-1-yl)-5-(methylsulfonyl)pyridine,
2-(5-(3-methoxy-4-methylphenyl)-1H-imidazol-1-yl)-5-(methylsulfonyl)pyridine,
2-(5-(4-chlorophenyl)-1H-imidazol-1-yl)-5-(methylsulfonyl)pyridine,
4-chloro-3-(1-(5-(methylsulfonyl)pyridin-2-yl)-1H-imidazol-5-yl)pyridine,
2,4-dichloro-3-(1-(5-(methylsulfonyl)pyridin-2-yl)-1H-imidazol-5-yl)pyridine,
2-(5-(2-chloro-4-methoxypyridin-3-yl)-1H-imidazol-1-yl)-5-(methylsulfonyl)pyridine,
3,4-dichloro-5-(1-(5-(methylsulfonyl)pyridin-2-yl)-1H-imidazol-5-yl)pyridine,
5-(methylsulfonyl)-2-(5-(4-propoxyphenyl)-1H-imidazol-1-yl)pyridine,
2-(5-(3,5-diethoxyphenyl)-1H-imidazol-1-yl)-5-(methylsulfonyl)pyridine,
2-(5-(4-ethoxyphenyl)-1H-imidazol-1-yl)-5-(methylsulfonyl)pyridine,
5-(methylsulfonyl)-2-(5-(4-nitrophenyl)-1H-imidazol-1-yl)pyridine,
2-(5-(4-(methylsulfinyl)phenyl)-1H-imidazol-1-yl)-5-(methylsulfonyl)pyridine,
2-(5-(4-(ethylsulfinyl)phenyl)-1H-imidazol-1-yl)-5-(methylsulfonyl)pyridine,
N,N-dimethyl-4-(1-(5-(methylsulfonyl)pyridin-2-yl)-1H-imidazol-5-yl)benzenamine,
2-(5-(4-fluorophenyl)-4-methyl-1H-imidazol-1-yl)-5-(methylsulfonyl)pyridine,
2-(4-chloro-5-(2,4-difluorophenyl)-1H-imidazol-1-yl)-5-(methylsulfonyl)pyridine,
2-(4-chloro-5-(2-chloro-4-methoxypyridin-3-yl)-1H-imidazol-1-yl)-5-(methylsulfonyl)pyridine,
3,4-dichloro-5-(4-chloro-1-(5-(methylsulfonyl)pyridin-2-yl)-1H-imidazol-5-yl)pyridine,
2-(4-chloro-5-(4-propoxyphenyl)-1H-imidazol-1-yl)-5-(methylsulfonyl)pyridine,
2-(4-chloro-5-(3,5-diethoxyphenyl)-1H-imidazol-1-yl)-5-(methylsulfonyl)pyridine,
2-(4-chloro-5-(4-ethoxyphenyl)-1H-imidazol-1-yl)-5-(methylsulfonyl)pyridine,
2-(4-chloro-5-(4-nitrophenyl)-1H-imidazol-1-yl)-5-(methylsulfonyl)pyridine,
2-(4-chloro-5-(4-(methylthio)phenyl)-1H-imidazol-1-yl)-5-(methylsulfonyl)pyridine,
2-(4-chloro-5-(4-(ethylthio)phenyl)-1H-imidazol-1-yl)-5-(methylsulfonyl)pyridine,
2-(4-chloro-5-(4-ethoxypyridin-3-yl)-1H-imidazol-1-yl)-5-(methylsulfonyl)pyridine,
2-(4-bromo-5-(4-fluorophenyl)-1H-imidazol-1-yl)-5-(methylsulfonyl)pyridine,
2-(5-(4-fluorophenyl)-4-methyl-1H-imidazol-1-yl)-5-(methylsulfonyl)pyridine,
2-(4-chloro-5-(4-(trifluoromethoxy)phenyl)-1H-imidazol-1-yl)-5-(methylsulfonyl)pyridine,
2-(4-chloro-5-(3,4-dichlorophenyl)-1H-imidazol-1-yl)-5-(methylsulfonyl)pyridine,
5-(4-chloro-5-(3-fluorophenyl)-1H-imidazol-1-yl)-2-(methylsulfonyl)pyridine,
5-(4-chloro-5-(3-fluoro-4-methylphenyl)-1H-imidazol-1-yl)-2-(methylsulfonyl)pyridine,
5-(4-chloro-5-(2-fluorophenyl)-1H-imidazol-1-yl)-2-(methylsulfonyl)pyridine,
5-(4-chloro-5-(4-(trifluoromethoxy)phenyl)-1H-imidazol-1-yl)-2-(methylsulfonyl)pyridine,
5-(5-(4-fluorophenyl)-1H-imidazol-1-yl)-2-(methylsulfonyl)pyridine,
2-(methylsulfonyl)-5-(5-p-tolyl-1H-imidazol-1-yl)pyridine, 5-(5-(2,4-difluorophenyl)-1H-imidazol-1-yl)-2-(methylsulfonyl)pyridine,
5-(5-(2,4-dichlorophenyl)-1H-imidazol-1-yl)-2-(methylsulfonyl)pyridine,
5-(5-(4-methoxyphenyl)-1H-imidazol-1-yl)-2-(methylsulfonyl)pyridine,
5-(5-(3-fluoro-4-methoxyphenyl)-1H-imidazol-1-yl)-2-(methylsulfonyl)pyridine,
5-(5-(3-fluorophenyl)-1H-imidazol-1-yl)-2-(methylsulfonyl)pyridine,
5-(5-(3-fluoro-4-methylphenyl)-1H-imidazol-1-yl)-2-(methylsulfonyl)pyridine,
5-(5-(2-fluorophenyl)-1H-imidazol-1-yl)-2-(methylsulfonyl)pyridine,
2-(methylsulfonyl)-5-(5-(4-(trifluoromethoxy)phenyl)-1H-imidazol-1-yl)pyridine,
4-methyl-3-(1-(6-(methylsulfonyl)pyridine-3-yl)-1H-imidazole-5-yl)pyridine,
5-(5-(2-fluoro-4-methoxyphenyl)-1H-imidazol-1-yl)-2-(methylsulfonyl)pyridine,
5-(5-(3-chloro-4-methyl)-1H-imidazol-1-yl)-2-(methylsulfonyl)pyridine,
5-(5-(3-methoxy-4-methylphenyl)-1H-imidazol-1-yl)-2-(methylsulfonyl)pyridine,
5-(5-(4-chlorophenyl)-1H-imidazol-1-yl)-2-(methylsulfonyl)pyridine,
5-(5-(4-chloropyridin-3-yl)-1H-imidazol-1-yl)-2-(methylsulfonyl)pyridine,
2,4-dichloro-3-(1-(6-(methylsulfonyl)pyridin-3-yl)-1H-imidazol-5-yl)pyridine,
2-chloro-4-methoxy-3-(1-(6-(methylsulfonyl)pyridin-3-yl)-1H-imidazol-5-yl)pyridine,
3,4-dichloro-5-(1-(6-(methylsulfonyl)pyridin-3-yl)-1H-imidazol-5-yl)pyridine,
2-(methylsulfonyl)-5-(5-(4-propoxyphenyl)-1H-imidazol-1-yl)pyridine,
5-(5-(3,5-diethoxyphenyl)-1H-imidazol-1-yl)-2-(methylsulfonyl)pyridine,
5-(5-(4-ethoxyphenyl)-1H-imidazol-1-yl)-2-(methylsulfonyl)pyridine,
2-(methylsulfonyl)-5-(5-(4-nitrophenyl)-1H-imidazol-1-yl)pyridine,
5-(5-(4-(methylsulfinyl)phenyl)-1H-imidazol-1-yl)-2-(methylsulfonyl)pyridine,
5-(5-(4-(ethylsulfinyl)phenyl)-1H-imidazol-1-yl)-2-(methylsulfonyl)pyridine,
N,N-dimethyl-4-(1-(6-(methylsulfonyl)pyridin-3-yl)-1H-imidazol-5-yl)benzenamine,
5-(5-(4-fluorophenyl)-4-methyl-1H-imidazol-1-yl)-2-(methylsulfonyl)pyridine,
5-(4-chloro-5-p-tolyl-1H-imidazol-1-yl)-2-(methylsulfonyl)pyridine,
5-(4-chloro-5-(2,4-difluorophenyl)-1H-imidazol-1-yl)-2-(methylsulfonyl)pyridine,
2-chloro-3-(4-chloro-1-(6-(methylsulfonyl)pyridin-3-yl)-1H-imidazol-5-yl)-4-methoxypyridine,
3,4-dichloro-5-(4-chloro-1-(6-(methylsulfonyl)pyridin-3-yl)-1H-imidazol-5-yl)pyridine,
5-(4-chloro-5-(4-propoxyphenyl)-1H-imidazol-1-yl)-2-(methylsulfonyl)pyridine,
5-(4-chloro-5-(3,5-diethoxyphenyl)-1H-imidazol-1-yl)-2-(methylsulfonyl)pyridine,
5-(4-chloro-5-(4-ethoxyphenyl)-1H-imidazol-1-yl)-2-(methylsulfonyl)pyridine,
5-(4-chloro-5-(4-nitrophenyl)-1H-imidazol-1-yl)-2-(methylsulfonyl)pyridine,
5-(4-chloro-5-(4-(methylthio)phenyl)-1H-imidazol-1-yl)-2-(methylsulfonyl)pyridine,
5-(4-chloro-5-(4-(ethylthio)phenyl)-1H-imidazol-1-yl)-2-(methylsulfonyl)pyridine,
3-(4-chloro-1-(6-(methylsulfonyl)pyridin-3-yl)-1H-imidazol-5-yl)-4-ethoxypyridine,
5-(4-bromo-5-(4-fluorophenyl)-1H-imidazol-1-yl)-2-(methylsulfonyl)pyridine,
5-(5-(4-fluorophenyl)-4-methyl-1H-imidazol-1-yl)-2-(methylsulfonyl)pyridine,
5-(4-chloro-5-(3,4-dichlorophenyl)-1H-imidazol-1-yl)-2-(methylsulfonyl)pyridine, and
5-(4-chloro-5-(3-chloro-4-methoxyphenyl)-1H-imidazol-1-yl)-2-(methylsulfonyl)pyridine.

In a further preferred embodiment of the present disclosure, the compound of formula (I) is selected from:
2-(4-chloro-5-phenyl-1H-imidazol-1-yl)-5-(methylsulfonyl)pyridine,
5-(methylsulfonyl)-2-(5-phenyl-1H-imidazol-1-yl)pyridine,
2-(4-chloro-5-(4-fluorophenyl)-1H-imidazol-1-yl)-5-(methylsulfonyl)pyridine,
2-(5-(4-fluorophenyl)-1H-imidazol-1-yl)-5-(methylsulfonyl)pyridine,
2-(4-chloro-5-p-tolyl-1H-imidazol-1-yl)-5-(methylsulfonyl)pyridine,
5-(methylsulfonyl)-2-(5-p-tolyl-1H-imidazol-1-yl)pyridine,
2-(4-chloro-5-(2,4-dichlorophenyl)-1H-imidazol-1-yl)-5-(methylsulfonyl)pyridine,
2-(5-(2,4-dichlorophenyl)-1H-imidazol-1-yl)-5-(methylsulfonyl)pyridine,
2-(4-chloro-5-(4-methoxyphenyl)-1H-imidazol-1-yl)-5-(methylsulfonyl)pyridine,
2-(5-(4-methoxyphenyl)-1H-imidazol-1-yl)-5-(methylsulfonyl)pyridine,
2-(4-chloro-5-(3-fluoro-4-methoxyphenyl)-1H-imidazol-1-yl)-5-(methylsulfonyl)pyridine,
2-(5-(3-fluoro-4-methoxyphenyl)-1H-imidazol-1-yl)-5-(methylsulfonyl)pyridine,
2-(4-chloro-5-(pyridin-3-yl)-1H-imidazol-1-yl)-5-(methylsulfonyl)pyridine,
5-(4-chloro-5-phenyl-1H-imidazol-1-yl)-2-(methylsulfonyl)pyridine,
2-(methylsulfonyl)-5-(5-phenyl-1H-imidazol-1-yl)pyridine,
5-(4-chloro-5-(4-methoxyphenyl)-1H-imidazol-1-yl)-2-(methylsulfonyl)pyridine,
5-(4-chloro-5-(3-fluoro-4-methoxyphenyl)-1H-imidazol-1-yl)-2-(methylsulfonyl)pyridine,
5-(4-chloro-5-(pyridin-3-yl)-1H-imidazol-1-yl)-2-(methylsulfonyl)pyridine, and
5-(4-chloro-5-(4-fluorophenyl)-1H-imidazol-1-yl)-2-(methylsulfonyl)pyridine.

In a further preferred embodiment of the present disclosure, the compound of formula (I) is selected from:
2-(4-chloro-5-phenyl-1H-imidazol-1-yl)-5-(methylsulfonyl)pyridine,
5-(methylsulfonyl)-2-(5-phenyl-1H-imidazol-1-yl)pyridine,
2-(4-chloro-5-(4-fluorophenyl)-1H-imidazol-1-yl)-5-(methylsulfonyl)pyridine,
2-(5-(4-fluorophenyl)-1H-imidazol-1-yl)-5-(methylsulfonyl)pyridine,
2-(4-chloro-5-p-tolyl-1H-imidazol-1-yl)-5-(methylsulfonyl)pyridine,
5-(methylsulfonyl)-2-(5-p-tolyl-1H-imidazol-1-yl)pyridine,
2-(4-chloro-5-(2,4-dichlorophenyl)-1H-imidazol-1-yl)-5-(methylsulfonyl)pyridine,
2-(5-(2,4-dichlorophenyl)-1H-imidazol-1-yl)-5-(methylsulfonyl)pyridine, 2-(4-chloro-5-(4-methoxyphenyl)-1H-imidazol-1-yl)-5-(methylsulfonyl)pyridine, 2-(5-(4-methoxyphenyl)-1H-imidazol-1-yl)-5-(methylsulfonyl)pyridine, 2-(4-chloro-5-(3-fluoro-4-methoxyphenyl)-1H-imidazol-1-yl)-5-(methylsulfonyl)pyridine, 2-(5-(3-fluoro-4-methoxyphenyl)-1H-imidazol-1-yl)-5-(methylsulfonyl)pyridine, 2-(4-chloro-5-(pyridin-3-yl)-1H-imidazol-1-yl)-5-(methylsulfonyl)pyridine, 5-(4-chloro-5-phenyl-1H-imidazol-1-yl)-2-(methylsulfonyl)pyridine, 5-(4-chloro-5-(4-methoxyphenyl)-1H-imidazol-1-yl)-2-(methylsulfonyl)pyridine, 5-(4-chloro-5-(3-fluoro-4-methoxyphenyl)-1H-imidazol-1-yl)-2-(methylsulfonyl)pyridine, and 5-(4-chloro-5-(4-fluorophenyl)-1H-imidazol-1-yl)-2-(methylsulfonyl)pyridine.

The present disclosure also relates to the salts, solvates, isomers and prodrugs of the compounds described above. A prodrug is any precursor of the compounds represented by the above formula (I), which can be decomposed in vivo and thereby releasing the compounds represented by the formula (I).

Some compounds represented by the formula (I) can have a chiral center, and therefore can produce different stereoisomers. The present disclosure also encompasses each of the stereoisomers and the mixtures thereof. Moreover, some compounds of the present disclosure may have cis and trans isomers. The present disclosure includes each of the geometric isomers and the mixtures thereof.

The present disclosure further encompasses pharmaceutical compositions consisting of an effective amount of a compound of formula (I) or its pharmaceutically acceptable salts, solvates, isomer or prodrugs, and one or more pharmaceutically acceptable excipients.

The present disclosure further encompasses uses of a compound of formula (I) or its pharmaceutically acceptable salts, solvates, isomers or prodrugs in the manufacture of a medicament for preventing or treating a disease mediated by cyclooxygenase, especially cyclooxygenase 2 (COX-2) in an animal and a human.

The present disclosure further encompasses uses of a compound of formula (I), or its pharmaceutically acceptable salts, solvates, isomers or prodrugs, in the manufacture of a medicament for treating inflammation, pain and fever in an animal or a human, including osteoarthritis, rheumatoid arthritis, acute pain, perioperative pain, post-operative pain, osphyalgia, shoulder periarthritis, neck shoulder wrist syndrome, tenosynovitis, dysmenorrheal, toothache, and etc.

The present disclosure further encompasses uses of a compound of formula (I), or its pharmaceutically acceptable salts, solvates, isomers or prodrugs, in the manufacture of a medicament for preventing or treating cancer, including colon cancer and breast cancer.

The present disclosure further encompasses uses of a compound of formula (I), or its pharmaceutically acceptable salts, solvates, isomers or prodrugs, in the manufacture of a medicament for preventing or treating depression in an animal and a human.

The present disclosure further encompasses use of a compound of formula (I), or its pharmaceutically acceptable salts, solvates, isomers or prodrugs, in the manufacture of the medicament for preventing or treating schizophrenia in an animal and a human.

The present disclosure further encompasses use of a compound of formula (I), or its pharmaceutically acceptable salts, solvates, isomers or prodrugs, in the manufacture of a medicament for preventing or treating cerebral infarction, epilepsy, neurodegenerative disease (e.g. Alzheimer's disease and senile dementia) and adenomatous polyp, especially familial adenomatous rectal polyp, in an animal and a human.

The animal described above includes canidae, equidae, feline, cervidae, and etc., such as a dog, a wolf, a cat, a panda, a horse and, a deer, and etc.

"Pharmaceutically acceptable" means that some carriers, vehicles, diluents, excipients, and/or salts formed therefrom are usually chemically and physically compatible with other ingredients constituting a pharmaceutical dosage form, and are physiologically compatible.

"Salts" and "pharmaceutically acceptable salts" refer to organic and inorganic salts of the compounds of formula (I), stereoisomers thereof, or prodrugs thereof. The salts can be obtained directly during the final separation and purification of the compounds. Alternatively, the salts can be obtained by reacting suitable organic or inorganic acids or bases with the compounds of formula (I) or their stereoisomers or prodrugs, and then by separating the salts. The commonly used salts include, such as, hydrobromide, hydrochloride, sulfate, bisulfate, nitrate, acetate, oxalate, besylate, palmitate, stearate, laurate, borate, benzoate, lactate, phosphate, tosylate, citrate, maleate, fumarate, succinate, tartrate, naphthoate, methanesulfonate, gluconate, lactobionate, dodecyl sulfonate and the like. These salts may further include cations in alkali or alkaline earth metals, such as sodium, lithium, potassium, calcium, magnesium and the other analogues, as well as non-toxic ammonium, quaternary ammonium, and ammonium cation, including, but not limited to, ammonium, tetramethylammonium, tetraethylammonium, methylamine, dimethylamine salt, trimethylamine salt, triethylamine salt, ethylamine and the other analogues. The details of the other examples are shown in a reference of the present application Berge, et al, J. Pharm. Sci., 66, 1-19 (1977).

Salts of a compound of formula (I) can be obtained by proper mixing of a solution of the compound of formula (I) with a desired acid or a desired base. These salts may form precipitates in a solution, which can be collected by filtration, or recovered after evaporation of the solvent.

Compounds of formula (I) can be provided in a non-solvated form or a solvated form in a pharmaceutically acceptable solvent such as water, and ethanol, and it can be expected that the present disclosure includes all the solvated and non-solvated forms.

A "prodrug" refers to a compound as a drug precursor, which can release an active drug via a chemical or physiological process (e.g., by placing in physiological pH or enzymatic action) in vivo after being administered to a subject. The discussion about synthesis and uses of prodrugs is provided in T. Higuchi and W. Stella's articles: "Prodrugs as Novel Delivery Systems," vol 14 of the ACS Symposium Series, and in Bioreversible Carriers in Drug Design, ed. Edward B. Roche, American Pharmaceutical Association and Pergamon Press, 1987. These two articles are incorporated herein by reference. A "prodrug" may also include a metabolic precursor of a compound of the present disclosure. Such a prodrug may be inactive when administering to a subject, but can be converted in vivo to a compound of the present disclosure. The prodrug can also be a naturally occurring or chemically synthesized compound.

Compounds of formula (I) can have an asymmetric or chiral center, and therefore can exist in different stereoisomers. It is envisaged that, all the isomers and the mixtures thereof including racemic mixtures, of the compounds of formula (I) are part of the present disclosure. In addition, all the geometric isomers and positional isomers are also encompassed. For example, if a compound of formula (I) contains a double bond, then both of the cis form and the trans from, and the mixtures thereof are also encompassed within the scope of the present disclosure.

The mixtures of diastereomers can be separated into their respective diastereomer based on their physical and chemical differences, using methods (e.g., chromatography and/or multi-step crystallization method) well known to those of ordinary skill in the art. The enantiomers can be separated by reacting with an optically active compound, converting the enantiomer mixtures into a diastereomer mixture, then separating the diastereomer, and converting (such as hydrolysizing) the respective diastereomer into the corresponding pure enantiomers. In addition, some compounds of formula (I) can be atropisomers (e.g., substituted biaryls), which are also a part of the present disclosure.

Compounds of formula (I) can also exist as tautomeric isomers in equilibrium, and all such forms are encompassed within the scope of the present disclosure.

In an embodiment of the present disclosure, the present disclosure comprises isotope-labeled compounds of formula (I). An isotope-labeled compound refers to a compound which is identical to a compound listed herein except that one or more atoms are substituted by an atom having an atomic mass or mass number different from that commonly seen in nature. The isotopes which can be introduced to the compounds of formula (I) include hydrogen, carbon, nitrogen, oxygen, phosphorus, fluorine and chlorine, i.e. $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$. Compounds of formula (I) containing the above-mentioned isotopes and/or other atom isotopes, their stereoisomers and prodrugs, and the pharmaceutically acceptable salts of the compounds, the stereoisomers or the prodrugs are encompassed within the scope of the present disclosure.

Some isotope-labeled compounds of formula (I), for example, the compounds labeled with radioisotopes such as $^3H$ and $^{14}C$, can be used in tissue distribution analysis of the compounds and/or the substrates. Tritium (i.e., $^3H$) and carbon-14 (i.e., $^{14}C$) isotopes are especially preferred for they are relatively easy to prepare and detect. In addition, some isotopes such as deuterium (i.e., $^2H$), can provide some therapeutic advantages due to a better metabolic stability (such as increasing in vivo half-life, or reducing dosing amount), and may be preferred under some situations. The isotope-labeled compounds of formula (I) can be prepared by methods well known to those of ordinary skill in the art, such as by replacing a non-isotope labeled reagent with an isotope-labeled reagent.

The present disclosure encompasses all the compounds disclosed above, especially the compounds of formula (I), encompassing those as independently present or in any compatible combination.

As described above, the compounds of the present disclosure primarily function by inhibiting cyclooxygenase 2 (COX-2 enzyme). Thus, they can be used for treating or preventing inflammation, pain and/or fever caused by various diseases or pathogens, and such diseases include: rheumatic fever, influenza or other viral infection symptoms, cold, waist and neck pain, dysmenorrhea, headache, toothache, courbature, neuralgia, synovitis, bursitis, arthritis including rheumatoid arthritis and juvenile arthritis, degenerative joint diseases including osteoarthritis, ankylosing spondylitis, lupus erythematosus, tendonitis, sprains strains and other injuries (such as injuries occurred in sports), pain after surgery or dental surgery and cancer pain. They can also be used for treating dermal inflammation such as psoriasis, eczema, burns and dermatitis.

The compounds of the present disclosure can also be used for treating other pathogenic infections mediated by COX-2 enzyme. For example, the compounds of formula (I) can inhibit cell proliferation, and therefore can be used for the treatment or prevention of cancers, particularly the cancers producing prostaglandin or expressing cyclooxygenase. The compounds of the present disclosure can be used for treating, for example, liver cancer, bladder cancer, pancreatic cancer, ovarian cancer, prostate cancer, cervical cancer, lung cancer, breast cancer and skin cancer, in particular digestive system cancers, such as colon cancer.

The compounds of the present disclosure can also be used for treating or preventing cerebral infarction, epilepsy, depression, schizophrenia and neurodegenerative diseases, such as Alzheimer's disease and dementia.

According to the activity of the products described herein, the present disclosure also includes a composition consisted of a compound of the present disclosure and a filler or other necessary excipients. The compounds of the present disclosure can be administered in any pharmaceutical formulations, and as is known in the art, the type of formulation mainly depends on the route of administration and pathology.

According to the present disclosure, solid compositions for oral use include tablets, suspensions, granules and capsules. In tablets, the active ingredients are mixed with at least one inert diluent (such as lactose, starch, mannitol, microcrystalline cellulose or calcium phosphate), binder (such as starch, gel, microcrystalline cellulose or polyvinyl pyrrolidone) and lubricant (such as magnesium stearate, stearic acid and talc). The tablets can be coated by known techniques to delay disintegration and absorption in the gastrointestinal tract, thereby providing for sustained release and controlled release. A gastrointestinal coating is prepared with sugar, mannitol, microcrystalline cellulose, acrylic resin and the like. The sustained release tablets may be produced with an excipient generating osmotic pressure, such as galacturonic acid polymers. The oral formulations may also be provided in the form of absorbable hard capsules, such as gelatin, where the controlled release effect can be achieved with the active compound together with an inert solid diluent and lubricant or paste material such as ethoxylated saturated glycerides. It may be also provided in the form of soft gel capsules, in which the active compound is mixed with water or oil medium, such as coconut oil, cotton oil, liquid paraffin or olive oil.

Powders and granules useful for reconstitution of a suspension with added water can be obtained by mixing the active compound with dispersing or wetting agents, suspending agents and one or more preservatives, in which the suspending agents may be sodium carboxymethyl cellulose, methyl cellulose, hydroxypropyl methyl cellulose, sodium alginate, polyvinylpyrrolidone, gum tragacanth, xanthan gum, gum arabic, and the preservatives may be the methyl parahydroxybenzoates or propyl ester. Additives such as sweeteners, flavoring agents and colorants may be also added.

Liquid formulations for oral use include emulsions, suspensions, syrups and elixirs, in which inert diluents, such as distilled water, ethanol, sorbitol, glycerol or propylene glycol, may typically be added. The compositions can also contain a co-excipient, such as a wetting agent, a suspending agent, a sweetener, a flavoring agent, a preservative, or a buffer.

According to the present disclosure, an injection formulation for injection is consisted of a sterile water-soluble or non-water-soluble solution, a suspension or emulsion dissolved in a suitable non-toxic solvent or diluent. Water-soluble solvent or suspending medium can be distilled water for injection, Green solution and isotonic sodium chloride solution. The non-water-soluble solvent or suspending medium can be propylene glycol, polyethylene glycol, vegetable oils (such as olive oil), or alcohol (such as ethanol). These components can also be used in combination with wetting agents, preservatives, emulsifiers and dispersing agents. They can be sterilized by any known methods, or can be prepared as a sterile solid composition, and then dissolved in water or any other sterile injectable medium before use. It can be also directly produced by sterile raw materials and be kept sterile during in the entire production process.

The dose and frequency of administration mainly depend on the types of animals and human, the nature and severity of the disease to be treated, the age and weight of the patient, and the route of administration. Typically, a daily dose for an adult animal or adult human is between 1 mg to 1000 mg, which can be administered in a single dose or multiple doses. However, for particular cases, the doses may exceed the above range. A person skilled in the art will decide an appropriate dose based on the specific condition of each case.

Another aspect of the present disclosure is to provide preparation processes of the compounds represented by formula (I). The compounds represented by formula (I) can be prepared according to the following reaction equations and discussions. Unless otherwise specified, in the following reaction equations and discussions, when $R^1$ represents hydrogen atom, halogen or $C_{1-5}$ alkyl, the following steps are comprised: $R^2$, $R^3$, $R^4$, $R^5$, $R^6$, $R^7$, X, Y are the groups defined above.

When $R^1$ represents hydrogen atom or $C_{1-5}$ alkyl, the process include the following steps:

a) reacting an imine of formula II with an isocyanide of formula III to obtain a compound of formula (IV), wherein X, Y, $R^2$, and $R^7$ in formula (II) are the groups defined above, wherein L in formula (III) represents a leaving group;

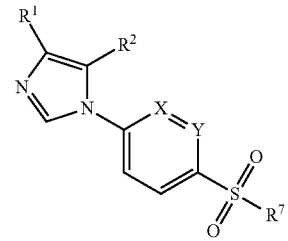

(II)

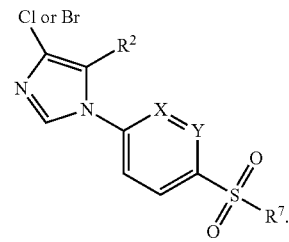

(III)

b) oxidizing a sulfide of formula (IV) to convert it to a compound of formula (V).

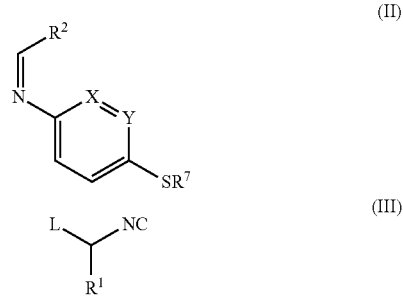

(IV)

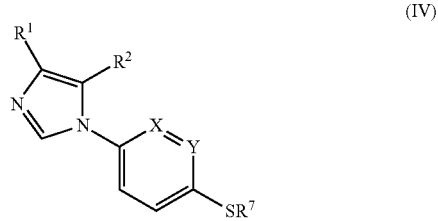

(V)

When $R^1$ represents halogen, the compound of formula (V) can be prepared using the above processes in which $R^1$ represents hydrogen, and then converted to a compound of formula (VI) by reacting with a halogenated reagent.

(VI)

It is obvious for those of skilled in the art that specific preparation methods for a compound can be slightly different depending on the chemical structure. Moreover, in most of the preparation processes set forth below, it is necessary to protect the unstable or reactive groups by conventional protecting groups. The properties of the said protecting groups and the preparation methods for their introduction or removal are well known in the art. (See, for example, Greene T. W. "Protective group in organic synthesis", John Wiley & Sons, New York, 1981)

The specific preparation methods are listed below, including Scheme 1 and Scheme 2, as follows:

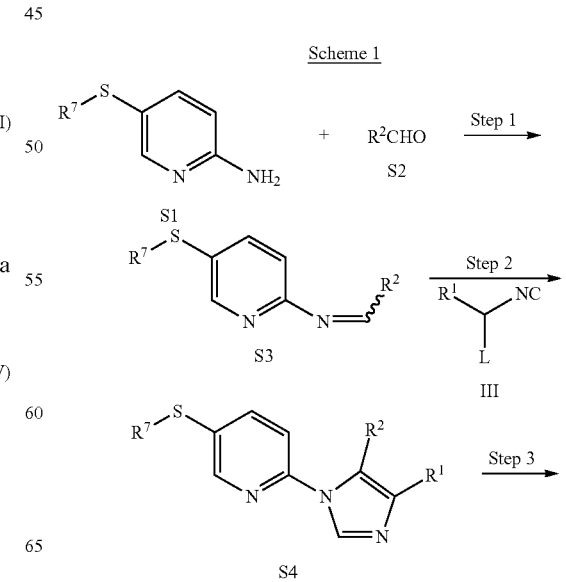

Scheme 1

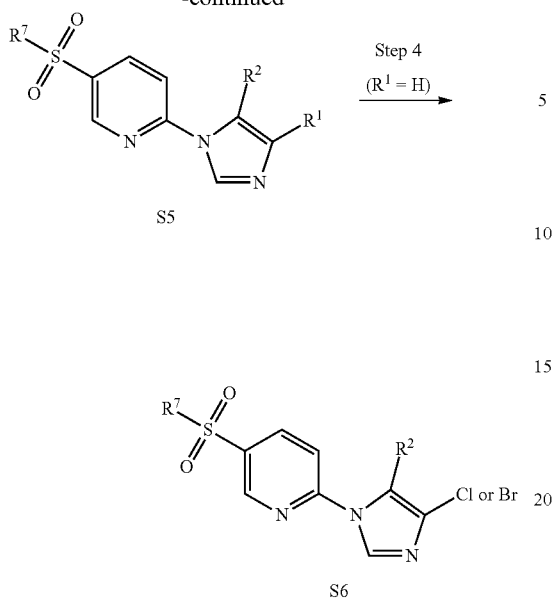

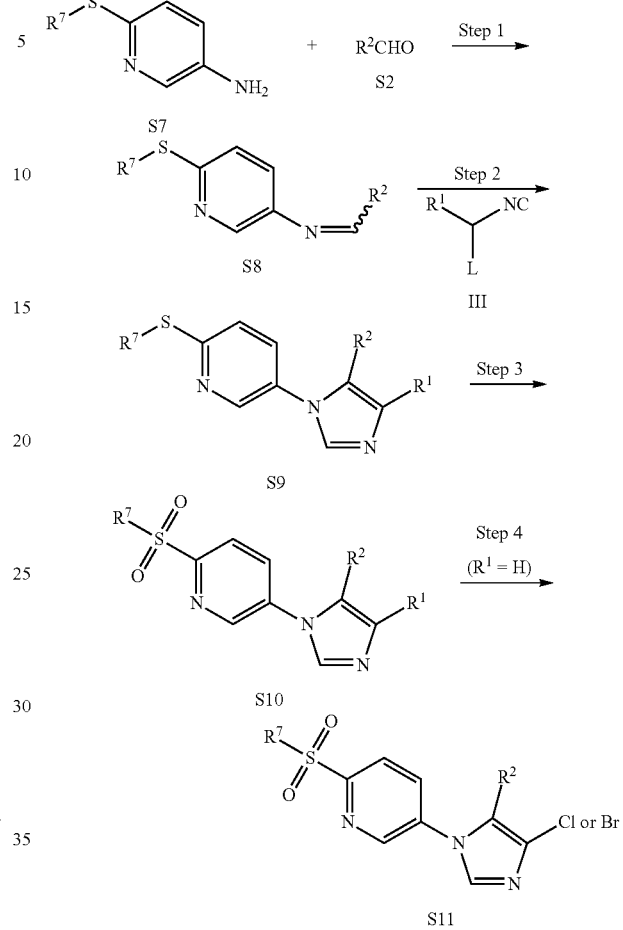

Scheme 2

Scheme 1 illustrates a method for synthesizing a compound of formula (I). According to the above Scheme 1, the compound of formula (S3) is obtained by the condensation reaction between the compound of formula (S1) and the compound of formula (S2) in an inert solvent. Suitable solvents in this reaction include alcohol (such as methanol, ethanol, and propanol), ether (such as 1,2-dimethoxyethane, 1,2-diethoxyethane, THF, DMF), or a mixture of the above alcohols and ethers. The reaction can be conducted in the presence of Lewis acid in a chemical equivalent amount or in a catalytic amount. The reaction is usually conducted at 0° C. to 100° C., preferably 50-80° C. for 10-30 hours.

The compound of formula (S4) is obtained by the reaction between the compound of formula (S3) and the compound of formula (III) in an inert solvent, wherein L represents a leaving group, for example, p-tosyl. Suitable solvents in the reaction include alcohol (such as methanol, ethanol, and propanol), ether (such as 1,2-dimethoxyethane, 1,2-diethoxyethane, THF, and DMF), or a mixture of the above alcohols and ethers. The reaction can be conducted in the presence of $K_2CO_3$, $Na_2CO_3$ in a chemical equivalent amount or in a catalytic amount. The reaction is usually conducted at 0° C. to 100° C., and the reflux reaction time is preferred to be 10-30 hours.

The compound of formula (S5) is obtained by the reaction between the compound of formula (S4) and oxidizing reagent in an inert solvent. The optimal solvent used in the reaction is dichloromethane. The optimal reagent used in the reaction is MCPBA (m-chloroperoxybenzoic acid). The reaction is usually conducted at −20° C. to 40° C., preferably 0° C.

When the substituent $R^1$ is a hydrogen atom, the compound of formula (S5) is converted into the compound of formula (S6) by reacting with a halogenated reagent. The preferred halogenated reagent is NCS (N-chlorosuccinimide). The reaction can be conducted in the presence of a catalyst such as AIBN (azobisisobutyronitrile), in a chemical equivalent amount or in a catalytic amount. The reaction is usually conducted at 0° C. to 100° C., preferably 50° C. to 80° C., for 10-30 hours.

Scheme 2 illustrates another method for synthesizing the compound represented by formula (I). According to the above Scheme 2, the compound of formula (S8) is obtained by the condensation reaction between the compound of formula (S7) and the compound of formula (S2) in an inert solvent. Suitable solvents in the reaction include alcohol (such as methanol, ethanol, and propanol), ether (such as 1,2-dimethoxyethane, 1,2-diethoxyethane, THF, and DMF), or a mixture of the above alcohols and ethers. The reaction can be conducted in the presence of Lewis acid in a chemical equivalent amount or in a catalytic amount. The reaction is usually conducted at 0° C. to 100° C., preferably 50-80° C., for 10-30 hours.

The compound of formula (S9) is obtained by the reaction between the compound of formula (S8) and the compound of formula (III) in an inert solvent, wherein L represents a leaving group, for example, p-tosyl. Suitable solvents in the reaction include alcohol (such as methanol, ethanol, and propanol), ether (such as 1,2-dimethoxyethane, 1,2-diethoxyethane, THF, and DMF), or a mixture of the above alcohols and ethers. The reaction can be conducted in the presence of $K_2CO_3$, $Na_2CO_3$ in a chemical equivalent amount or in a catalytic amount. The reaction is usually conducted at 0° C. to 100° C., and the reflux reaction time is preferred to be 10-30 hours.

The compound of formula (S10) is obtained by the reaction between the compound of formula (S9) and oxidizing reagent in an inert solvent. The preferable solvent used in the reaction is dichloromethane. The optimal oxidizing reagent used in the reaction is MCPBA (m-chloroperoxybenzoic acid). The reaction is usually conducted at −20° C. to 40° C., preferably 0° C.

When the substituent $R^1$ is a hydrogen atom, the compound of formula (S10) is converted into the compound of formula (S11) by reacting with a halogenated reagent. The optimal halogenated reagent is NCS (chlorosuccinimide). The reaction can be conducted in the presence of a chemical equivalent or a catalytic amount of catalyst, such as AIBN (azobisisobutyronitrile). The reaction is usually conducted at 0° C. to 100° C., preferably 50° C. to 80° C., for 10-30 hours.

EXAMPLES

The following examples illustrate the preparation of a compound of formula (I) in details. These detailed methods are within the scope of the present disclosure, and the method for the illustration of the above general synthetic route is also a part of the present disclosure. These disclosures described in detail are for illustration only, and are not intended to limit the scope of the present disclosure.

MeOH: methanol
NaSMe: sodium methanethiolate
EtOAc: ethyl acetate
$Na_2SO_4$: sodium sulfate
AcOH: acetic acid
$NaHCO_3$: sodium bicarbonate
$Ti(OiPr)_4$: titanium isopropoxide
THF: tetrahydrofuran
$K_2CO_3$: Potassium carbonate
DME: dimethoxyethane
TosMIC: toluenesulfonylmethyl isocyanide
mCPBA: meta-chloro peroxybenzoic acid
DCM: dichloromethane
$Na_2S_2O_3$: sodium thiosulfate
NCS: N-chlorosuccinimide
$CCl_4$: Carbon tetrachloride
AIBN: azobisisobutyronitrile The preparation method of Examples 1-7 are set forth below, and not intended to limit the scope of the present disclosure. The chemical structure formulas and chemical names in Examples 1-7 are shown in Table 1, and the structure confirmation data is shown in Table 2:

TABLE 1

The structure formulas and chemical names in Examples 1-7

| Example | Formula | Chemical Name (English) | Chemical Name (Chinese) |
|---|---|---|---|
| Example 1 (Compound 1) | | 2-(4-chloro-5-phenyl-1H-imidazol-1-yl)-5-(methylsulfonyl) pyridine | 2-(4-chloro-5-phenyl-1H-imidazol-1-yl)-5-(methylsulfonyl) pyridine |
| Example 1 (Compound 1E) | | 5-(methylsulfonyl)-2-(5-phenyl-1H-imidazol-1-yl) pyridine | 5-(methylsulfonyl)-2-(5-phenyl-1H-imidazol-1-yl) pyridine |
| Example 2 (Compound 2) | | 2-(4-chloro-5-(4-fluorophenyl)-1H-imidazol-1-yl)-5-(methylsulfonyl) pyridine | 2-(4-chloro-5-(4-fluorophenyl)-1H-imidazol-1-yl)-5-(methylsulfonyl) pyridine |

TABLE 1-continued

The structure formulas and chemical names in Examples 1-7

| Example | Formula | Chemical Name (English) | Chemical Name (Chinese) |
|---|---|---|---|
| Example 2 (Compound 2E) | 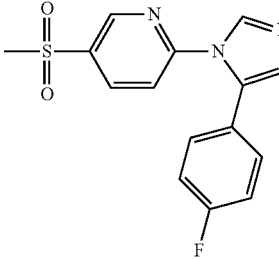 | 2-(5-(4-fluorophenyl)-1H-imidazol-1-yl)-5-(methylsulfonyl) pyridine | 2-(5-(4-fluorophenyl)-1H-imidazol-1-yl)-5-(methylsulfonyl) pyridine |
| Example 3 | 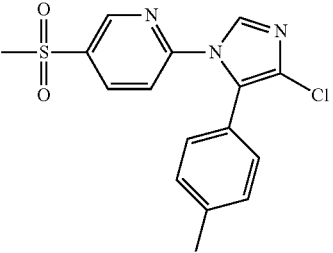 [SMILES: Cc1ccc(-c2c(Cl)ncn2-c2ccc(S(C)(=O)=O)cn2)cc1] | 2-(4-chloro-5-p-tolyl-1H-imidazol-1-yl)-5-(methylsulfonyl) pyridine | 2-(4-chloro-5-p-tolyl-1H-imidazol-1-yl)-5-(methylsulfonyl) pyridine |
| Example 3 (Compound 3E) | 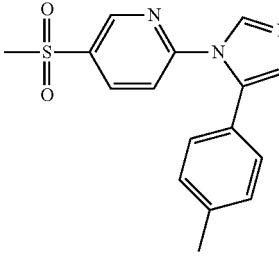 | 5-(methylsulfonyl)-2-(5-p-tolyl-1H-imidazol-1-yl) pyridine | 5-(methylsulfonyl)-2-(5-p-tolyl-1H-imidazol-1-yl) pyridine |
| Example 4 (Compound 4) | 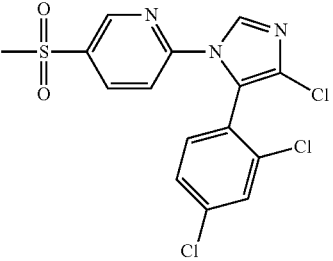 [SMILES: CS(=O)(=O)c1ccc(-n2cnc(Cl)c2-c2ccc(Cl)cc2Cl)nc1] | 2-(4-chloro-5-(2,4-dichlorophenyl)-1H-imidazol-1-yl)-5-(methylsulfonyl) pyridine | 2-(4-chloro-5-(2,4-dichlorophenyl)-1H-imidazol-1-yl)-5-(methylsulfonyl) pyridine |
| Example 4 (Compound 4E) | 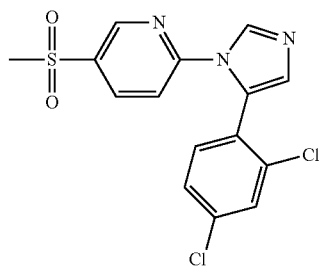 [SMILES: CS(=O)(=O)c1ccc(-n2cncc2-c2ccc(Cl)cc2Cl)nc1] | 2-(5-(2,4-dichlorophenyl)-1H-imidazol-1-yl)-5-(methylsulfonyl) pyridine | 2-(5-(2,4-dichlorophenyl)-1H-imidazol-1-yl)-5-(methylsulfonyl) pyridine |

TABLE 1-continued

The structure formulas and chemical names in Examples 1-7

| Example | Formula | Chemical Name (English) | Chemical Name (Chinese) |
|---|---|---|---|
| Example 5 (Compound 5) | | 2-(4-chloro-5-(4-methoxyphenyl)-1H-imidazol-1-yl)-5-(methylsulfonyl) pyridine | 2-(4-chloro-5-(4-methoxyphenyl)-1H-imidazol-1-yl)-5-(methylsulfonyl) pyridine |
| Example 5 (Compound 5E) | | 2-(5-(4-methoxyphenyl)-1H-imidazol-1-yl)-5-(methylsulfonyl) pyridine | 2-(5-(4-methoxyphenyl)-1H-imidazol-1-yl)-5-(methylsulfonyl) pyridine |
| Example 6 (Compound 6) | | 2-(4-chloro-5-(3-fluoro-4-methoxyphenyl)-1H-imidazol-1-yl)-5-(methylsulfonyl) pyridine | 2-(4-chloro-5-(3-fluoro-4-methoxyphenyl)-1H-imidazol-1-yl)-5-(methylsulfonyl) pyridine |
| Example 6 (Compound 6E) | | 2-(5-(3-fluoro-4-methoxyphenyl)-1H-imidazol-1-yl)-5-(methylsulfonyl) pyridine | 2-(5-(3-fluoro-4-methoxyphenyl)-1H-imidazol-1-yl)-5-(methylsulfonyl) pyridine |
| Example 7 (Compound 7) | | 2-(4-chloro-5-(pyridin-3-yl)-1H-imidazol-1-yl)-5-(methylsulfonyl) pyridine | 2-(4-chloro-5-(pyridin-3-yl)-1H-imidazol-1-yl)-5-(methylsulfonyl) pyridine |

TABLE 2

The structure confirmation data of Examples 1-7

| Compound | R¹ | R² | ¹H-NMR (CDCl₃), δ | LC-MS m/z [M⁺ + 1] |
|---|---|---|---|---|
| 1 | Cl | phenly | 300 MHz: 3.12 (3H, s), 6.78 (1H, dd), 7.28 (2H, m), 7.44 (3H, m), 8.06 (1H, dd), 8.25 (1H, s), 9.03 (1H, dd) | 335 |
| 1E | H | phenyl | 300 MHz: 33.14 (3H, s), 6.90 (2H, d), 7.24 (2H, m), 7.36 (3H, m), 8.07 (1H, m), 8.31 (1H, s), 9.05 (1H, d) | 300 |
| 2 | Cl | 4-fluorophenyl | 400 MHz: 33.14 (3H, s), 6.82 (1H, d), 7.17-7.13 (2H, m), 7.31-7.27 (2H, m), 8.10 (1H, dd), 8.23 (1H, s), 9.04 (1H, d). | 353 |
| 2E | H | 4-fluorophenyl | 400 MHz: 33.08 (3H, s), 6.85 (1H, d), 7.01-7.05 (2H, m), 7.14-7.19 (3H, m), 8.05 (1H, dd), 8.22 (1H, s), 8.98 (1H, d) | 318 |
| 3 | Cl | 4-methyl phenyl | 400 MHz: 2.41 (3H, s), 3.13 (3H, s), 6.80 (1H, d), 7.18 (1H, d), 7.25 (2H, d), 8.05 (1H, dd), 8.25 (1H, s), 9.03 (1H, d) | 349 |
| 3E | H | 4-methyl phenyl | 400 MHz: 2.39 (3H, s), 3.14 (3H, s), 6.91 (1H, d), 7.12 (2H, d), 7.19 (2H, d), 7.20 (1H, s), 8.07 (1H, dd), 8.30 (1H, s), 9.05 (1H, d) | 314 |
| 4 | Cl | 2,4-dichlorobenzene | 400 MHz: 3.13 (3H, s), 6.92 (1H, d), 7.42 (2H, d), 7.49 (1H, s), 8.16 (1H, dd), 8.33 (1H, s), 8.97 (1H, d) | 403 |
| 5 | Cl | 4-methoxyphenyl | 400 MHz: 3.13 (3H, s), 3.86 (3H, s), 6.82 (1H, d), 6.97 (2H, d), 7.21-7.23 (2H, m), 8.06 (1H, d), 8.24 (1H, s), 9.03 (1H, s) | 365 |
| 5E | H | 4-methoxyphenyl | 400 MHz: 3.14 (3H, s), 3.85 (3H, s), 6.90-6.93 (3H, m), 7.15-7.17 (3H, m), 8.07 (1H, dd), 8.28 (1H, s), 9.05 (1H, d) | 330 |
| 6 | Cl | 3-fluoro-4-methoxyphenyl | 400 MHz: 3.15 (3H, s), 3.95 (3H, s), 6.85 (1H, d, 7.00-7.07 (3H, m), 8.11 (1H, dd), 8.22 (1H, s), 9.04 (1H, d) | 383 |
| 6E | H | 3-fluoro-4-methoxyphenyl | 400 MHz: 3.18 (3H, s), 3.96 (3H, s), 6.96-7.03 (3H, m), 7.23-7.26 (2H, m), 8.16 (1H, dd), 8.31 (1H, s), 9.08 (1H, s) | 348 |
| 7 | Cl | 3-pyridyl | 400 MHz: 3.15 (3H, s), 6.93 (1H, d), 7.40-7.43 (1H, m), 7.71 (1H, d), 8.15-8.18 (1H, m), 8.22 (1H, s), 8.51 (1H, s), 8.66 (1H, d), 9.03 (1H, d) | 336 |

The synthetic route of Examples 1-7 is shown as below:

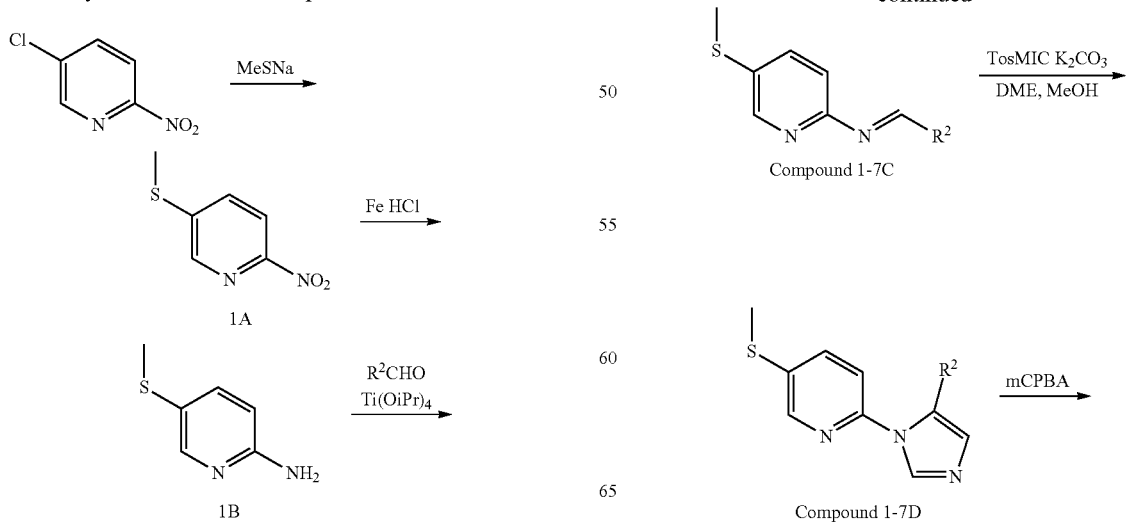

-continued

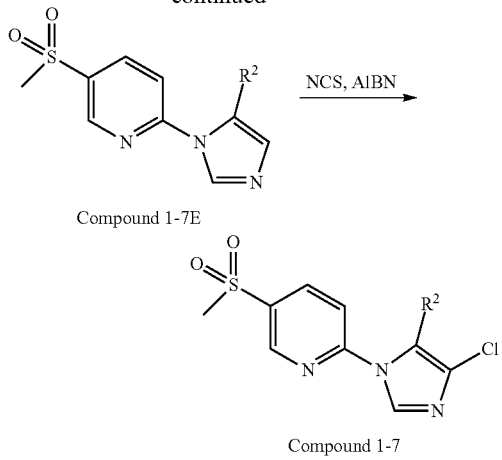

Compound 1-7E

Compound 1-7

Example 1

The Preparation of Compound 2-(4-chloro-5-phenyl-1H-imidazol-1-yl)-5-(methylsulfonyl)pyridine (Compound 1)

Step A. Preparation of Compound 5-(methylthio)-2-nitropyridine (Compound 1 A)

The methanol solution (2000 mL) of methyl sodium sulfide (150 g) was added dropwise into the methanol solution (4000 mL) of 5-chloro-2-nitropyridine (300 g), and the reaction temperature was kept below 0° C. After completing the dropping, the reactant was heated to room temperature, and stirred overnight. The solvent of the reaction mixture was discarded and 5 liters of water was added into the residue, then extracted with ethyl acetate. The organic layer was washed with saturated NaCl solution, and dried with anhydrous sodium sulfate. The yellow and solid target compound (270 g) was obtained by filtration and concentration under reduced pressure. $^1$H-NMR (300 MHz, CDCl$_3$) δ 2.61 (3H, s), 7.73 (1H, dd), 8.18 (1H, d), 8.40 (1H, d). LC-MS m/z: 171 [M$^+$+1].

Step B. Preparation of Compound 5-(methylthio)-2-aminopyridine (Compound 1 B)

5-(methylthio)-2-nitropyridine (270 g), iron powder (600 g), acetic acid (500 mL) and water (2 L) were heated to reflux for 4 hours. Then saturated sodium bicarbonate solution (6 L) was added into the reaction mixture. The reaction mixture was filtered, and the filtrate was extracted with ethyl acetate. The organic phase was washed with saturated NaCl solution, and dried with anhydrous sodium sulfate. After filtration, the residual solution was removed under reduced pressure to obtain the target compound (185 g). $^1$H-NMR (300 MHz, CDCl$_3$): δ 2.39 (3H, s), 4.49 (2H, brs), 6.47 (1H, d), 7.50 (1H, dd), 8.11 (1H, d). LC-MS m/z: 141 [M$^+$+1].

Step C. Preparation of Compound N-benzal-5-(methylthio)pyridine-2-amine (Compound 1C)

5-(methylthio)-2-aminopyridine (185 g) was dissolved in 2 L tetrahydrofuran, and then 500 mL titanate tetraisopropyl and benzaldehyde (155 g) were added. The reaction mixture was heated for reflux overnight, then cooled to room temperature, and 10 L water was added. The reaction mixture was extracted with ethyl acetate, the organic phase was washed with saturated NaCl solution, and dried with anhydrous sodium sulfate. After filtration, the residual solution was removed under reduced pressure to obtain the target compound (200 g).

Step D. Preparation of Compound 5-(methylthio)-2-(5-phenyl-1H-imidazol-1-yl)pyridine (Compound 1 D)

N-benzal-5-(methylthio)pyridine-2-amine (200 g), tosylmethyl isocyanide (255 g), potassium carbonate (255 g), methanol (3 L) and dimethoxyethane (2 L) were refluxed overnight. The reactant was cooled to room temperature, 10 L water was added and extracted with ethyl acetate. The organic phase was washed with saturated NaCl solution, and dried with anhydrous sodium sulfate. The solvent was removed by filtration and reducing pressure. The crude product was purified by column chromatography to obtain the brown solid target compound (118 g, 50% yield). $^1$H-NMR (300 MHz, CDCl$_3$): δ 2.52 (3H, s), 6.74-6.77 (1H, dd), 7.18-7.22 (3H, m), 7.30-7.33 (3H, m), 7.45-7.48 (1H, dd), 8.05-8.05 (1H, d), 8.38-8.39 (1H, d). LC-MS m/z: 268 [M$^+$+1].

Step E. Preparation of Compound 5-(methylsulfonyl)-2-(5-phenyl-1H-imidazol-1-yl)pyridine (Compound 1 E)

M-chloroperoxybenzoic acid (230 g) and 5-(methylthio)-2-(5-phenyl-1H-imidazol-1-yl)pyridine (118 g) were dissolved in 3 L dichloromethane, and stirred to react for 2 hours at 0° C. After the reaction was complete, 1000 mL saturated Na$_2$S$_2$O$_3$ solution was added. The mixture was extracted with dichloromethane, the organic phase was washed with saturated NaCl solution, and dried with anhydrous sodium sulfate. After filtration and concentration, the crude product was purified by column chromatography to obtain the target compound (50 g). $^1$H-NMR (300 MHz, CDCl$_3$): δ 3.14 (3H, s), 6.90 (1H, d), 7.24 (3H, m), 7.39 (3H, m), 8.06 (1H, dd), 8.30 (1H, s), 9.05 (1H, d); LC-MS m/z: 300 [M$^+$+1], purity (HPLC)>95%.

Step. F Preparation of Compound 2-(4-chloro-5-phenyl-1H-imidazol-1-yl)-5-(methylsulfonyl)pyridine (Compound 1)

5-(methylsulfonyl)-2-(5-phenyl-1H-imidazol-1-yl)pyridine (50 g), N-chlorosuccinimide (20 g) and azo-bis-isobutyronitrile (500 mg) were dissolved in 3 L tetrachloromethane to allow reflux overnight. The reaction mixture was cooled to room temperature, and the residual solvent was removed under reduced pressure. The crude product was purified by column chromatography to obtain the target compound (15 g). $^1$H-NMR (300 MHz, CDCl$_3$): δ 3.12 (3H, s), 6.78 (1H, dd), 7.28 (2H, m), 7.44 (3H, m), 8.06 (1H, dd), 8.25 (1H, s), 9.03 (1H, dd); LC-MS m/z: 335 [M$^+$+1], purity (HPLC) >95%.

Example 2

Preparation of 2-(4-chloro-5-(4-fluorophenyl)-1H-imidazol-1-yl)-5-(methylsulfonyl)pyridine (Compound 2)

Step A and Step B were the Same as Example 1

Step C. Synthesis of Compound 2C

Compound 1B (340 mg, 2.4 mmol) was dissolved in THF (20 mL), and then 4-fluorobenzaldehyde (301 mg, 2.4 mmol)

and Ti(OiPr)$_4$ (2.1 mL) were added, respectively. The reaction mixture was heated to reflux for 2 days, and then cooled to room temperature. The reaction mixture was poured into saturated NaHCO$_3$ solution. The mixture was extracted with ethyl acetate, and the organic layer was washed with saturated NaCl solution, dried with anhydrous sodium sulfate. The filtered and concentrated product 2C (678 mg, crude) was directly used in the next reaction step without purification.

Step D. Synthesis of Compound 2D

Compound 2C (678 mg, 4.2 mmol) was dissolved in DMF (10 mL), and methanol solution (25 mL) of TosMIC (806 mg, 4.2 mmol) and K$_2$CO$_3$ (951 mg, 7.0 mmol) was added. The mixture was heated to reflux for 2 days, and then cooled to room temperature. The reaction mixture was poured into water, and extracted with ethyl acetate. The organic layer was washed with saturated NaCl solution, dried with anhydrous sodium sulfate. After filtration, the solvent was evaporated to dryness to obtain crude product, which was purified by silica gel column to obtain yellow solid compound 2D (160 mg, 20%). $^1$H-NMR (400 MHz, CDCl$_3$): δ 2.51 (3H, s), 6.75 (1H, d), 7.21 (1H, d), 7.26-7.29 (3H, m), 7.40 (1H, s), 7.48-7.51 (1H, m), 8.16 (1H, d), 8.30 (1H, d); LC-MS: 286 [M$^+$+1].

Step E. Synthesis of Compound 2E

Compound 2D (160 mg, 0.56 mmol) was dissolved in DMF (20 mL), and DMF solution (10 mL) of mCPBA (430 mg, 2.8 mmol) was added at −20° C., and the reaction mixture was stirred for 5 hours at −20° C. After the reaction was complete, saturated aqueous solution of Na$_2$S$_2$O$_3$ (30 mL) was added at −20° C. The mixture was extracted with DCM (2×50 mL), and the organic layer was washed with saturated NaCl solution, dried with anhydrous sodium sulfate. After filtration, the solvent was evaporated to dryness to obtain yellow solid compound 2E (192 mg, crude), which was directly used in the next reaction step without purification. $^1$H-NMR (400 MHz, CDCl$_3$): δ 3.08 (3H, s), 6.85 (1H, d), 7.01-7.05 (2H, m), 7.14-7.19 (3H, m), 8.05 (1H, dd), 8.22 (1H, s), 8.98 (1H, d); LC-MS: 318 [M$^+$+1].

Step F. Synthesis of Compound 2

The crude product of Compound 2E (192 mg, 0.56 mmol) was dissolved in DCM (10 mL), and pyridine solution (10 mL) of NCS (112 mg, 0.84 mmol) and AIBN (5.0 mg) was added. The mixture was stirred overnight at room temperature. After filtration and solvent evaporation to dryness, the crude product was purified by silica gel column to obtain Compound 2 (42 mg, 21%). $^1$H-NMR (400 MHz, CDCl$_3$): δ 3.14 (3H, s), 6.82 (1H, d), 7.17-7.13 (2H, m), 7.31-7.27 (2H, m), 8.10 (1H, dd), 8.23 (1H, s), 9.04 (1H, d). Purity (HPLC) >95%, LC-MS: 353 [M$^+$+1].

Example 3

The Preparation of 5-(methylsulfonyl)-2-(5-p-methoxybenzyl-1H-imidazol-1-yl)pyridine (Compound 3)

Step A and Step B were the Same as Example 1

Step C. Synthesis of Compound 3C

Compound 1B (490 mg, 3.5 mmol) was dissolved in THF (30 mL), and 4-tolualdehydes (420 mg, 3.5 mmol) and Ti(O-iPr)$_4$ (5.2 mL) were added, respectively. The reaction mixture was heated to reflux for 1 day, and then cooled to room temperature. The reaction mixture was poured into saturated NaHCO$_3$ solution. The mixture was extracted with ethyl acetate, and the organic layer was washed with saturated NaCl solution, and dried with anhydrous sodium sulfate. After filtration, the solvent was evaporated to dryness to obtain compound 3C (1.10 g, crude), which was directly used in the next reaction step without purification.

Step D. Synthesis of Compound 3D

Compound 3C (800 mg, 3.0 mmol) was dissolved in DME (10 mL), and MeOH solution (25 mL) of TosMIC (780 mg, 4.5 mmol) and K$_2$CO$_3$ (1.00 g, 7.5 mmol) was added. The mixture was heated to reflux for 1 day, and then cooled to room temperature. The reaction mixture was poured into water. The mixture was extracted with ethyl acetate, and the organic layer was washed with saturated NaCl solution, and dried with anhydrous sodium sulfate and filtered. The solvent was evaporated to dryness to obtain crude product, which was purified by silica gel column to obtain yellow solid Compound 3D (100 mg, 12%). $^1$H-NMR (400 MHz, CDCl$_3$): δ 2.36 (3H, s), 2.53 (3H, s), 6.76 (1H, d), 7.07-7.18 (5H, m), 7.46-7.49 (1H, m), 8.05 (1H, s), 8.39 (1H, d); LC-MS: 282 [M$^+$+1].

Step E. Synthesis of Compound 3E

Compound 3D (100 mg, 0.36 mmol) was dissolved in DMF (20 mL), and DMF solution (10 mL) of mCPBA (300 mg, 1.8 mmol) was added at −20° C., and the reaction mixture was stirred for 5 hours at −20° C. After the reaction was complete, saturated aqueous solution of Na$_2$S$_2$O$_3$ (30 mL) was added at −20° C. The mixture was extracted with DCM (2×50 mL), and the organic layer was washed with saturated NaCl solution, and dried with anhydrous sodium sulfate. After filtration, the solvent was evaporated to dryness to obtain yellow oily Compound 3E (70 mg, crude, 62%), which was directly used in the next reaction step without purification. $^1$H-NMR (400 MHz, CDCl$_3$): δ 2.39 (3H, s), 3.14 (3H, s), 6.91 (1H, d), 7.12 (2H, d), 7.19 (2H, d), 7.20 (1H, s), 8.07 (1H, dd), 8.30 (1H, s), 9.05 (1H, d); LC-MS: 314 [M$^+$+1].

Step F. Synthesis of Compound 3

Compound 3E (70 mg, 0.22 mmol) was dissolved in DCM (10 mL), and pyridine solution (10 mL) of NCS (32 mg, 0.25 mmol) and AIBN (5.0 mg) was added. The mixture was stirred overnight at room temperature. After solvent evaporation to dryness, the crude product was purified by silica gel column to obtain Compound 3 (19 mg, 25%). $^1$H-NMR (400 MHz, CDCl$_3$): δ2.41 (3H, s), 3.13 (3H, s), 6.80 (1H, d), 7.18 (2H, d), 7.25 (2H, d), 8.05 (1H, dd), 8.25 (1H, s), 9.03 (1H, d). Purity HPLC>95%, LC-MS: 349 [M$^+$+1].

Example 4

Preparation of 2-(4-chloro-5-(2,4-dichlorophenyl)-1H-imidazol-1-yl)-5-(methylsulfonyl)pyridine (Compound 4)

Step A and Step B were the Same as Example 1

Step C. Synthesis of Compound 4C

Compound 1B (340 mg, 2.4 mmol) was dissolved in THF (30 mL), and 2,4-dichlorobenzaldehyde (425 mg, 2.4 mmol)

and Ti(OiPr)$_4$ (2.2 mL) were added, respectively. The reaction mixture was heated to reflux for 2 days, and then cooled to room temperature, and poured into saturated NaHCO$_3$ aqueous solution. The mixture was extracted with ethyl acetate, and the organic layer was washed with saturated NaCl solution, dried with anhydrous sodium sulfate and filtered. The solvent was evaporated to dryness to obtain Compound 4C (738 mg, crude), which was directly used in the next reaction step without purification.

Step D. Synthesis of Compound 4D

Compound 4C (738 mg, 2.5 mmol) was dissolved in DME (10 mL), and MeOH solution (25 mL) of TosMIC (727 mg, 3.8 mmol) and K$_2$CO$_3$ (857 mg, 7.5 mmol) was added. The mixture was heated to reflux for 1 day, and then cooled to room temperature. The reaction mixture was poured into water. The mixture was extracted with ethyl acetate, and the organic layer was washed with saturated NaCl solution, and dried with anhydrous sodium sulfate and filtered. The solvent was evaporated to dryness to obtain crude product, which was purified by silica gel column to obtain yellow solid Compound 4D (467 mg, 56%). $^1$H-NMR (400 MHz, CDCl$_3$): δ 3.13 (3H, s), 6.97 (1H, d), 7.23-7.26 (2H, d), 7.37 (1H, s), 7.44 (1H, s), 8.15 (1H, dd), 8.37 (1H, s), 8.96-8.97 (1H, d); LC-MS: 336 [M$^+$+1].

Step E. Synthesis of Compound 4E

Compound 4D (450 mg, 1.30 mmol) was dissolved in DMF (20 mL), and DMF solution (10 mL) of mCPBA (1.20 g, 6.5 mmol) was added at −20° C., and the reaction mixture was stirred for 5 hours at −20° C. After the reaction was complete, saturated aqueous solution of Na$_2$S$_2$O$_3$ (30 mL) was added at −20° C. The mixture was extracted with DCM (2×50 mL), and the organic layer was washed with saturated NaCl solution, dried with anhydrous sodium sulfate and filtered. The solvent was evaporated to dryness to obtain yellow oily Compound 4E (234 mg, 48%), which was directly used in the next reaction step without purification. LC-MS: 368 [M$^+$+1].

Step F. Synthesis of Compound 4

Compound 4E (234 mg crude, 0.64 mmol) was dissolved in DCM (10 mL), and pyridine solution (10 mL) of NCS (127 mg, 0.96 mmol) and AIBN (5.0 mg) was added. The mixture was stirred overnight at room temperature. After solvent evaporation to dryness, the crude product was purified by silica gel column (PE/EA=1:1) to obtain Compound 4 (16 mg, 6%). $^1$H-NMR (400 MHz, CDCl$_3$): δ 3.13 (3H, s), 6.92 (1H, d), 7.42 (2H, d), 7.49 (1H, s), 8.16 (1H, dd), 8.33 (1H, s), 8.97 (1H, d). Purity (HPLC)>95%, LC-MS: 403 [M$^+$+1].

Example 5

Preparation of 2-(4-chloro-5-(4-methoxyphenyl)-1H-imidazol-1-yl)-5-(methylsulfonyl)pyridine (Compound 5)

Step A and Step B were the Same as Example 1

Step C. Synthesis of Compound 5C

Compound 1B (560 mg, 4.0 mmol) was dissolved in THF (30 mL), and 4-methoxybenzaldehyde (540 mg, 4.0 mmol) and Ti(OiPr)$_4$ (2.9 mL) were added, respectively. The reaction mixture was heated to reflux for 1 day, and then cooled to room temperature. The reaction mixture was poured into saturated NaHCO$_3$ solution. The mixture was extracted with ethyl acetate, and the organic layer was washed with saturated NaCl solution, and dried with anhydrous sodium sulfate. The filtered and concentrated product 5C (1.01 g, crude) was directly used in the next reaction step without purification.

Step D. Synthesis of Compound 5D

Compound 5C (1.01 g, 4.0 mmol) was dissolved in DMF (10 mL), and the MeOH solution (25 mL) of TosMIC (1.2 g, 6.0 mmol) and K$_2$CO$_3$ (1.4 g, 10 mmol) was added. The mixture was heated to reflux for 1 day, and then cooled to room temperature. The reaction mixture was poured into water. The mixture was extracted with ethyl acetate, and the organic layer was washed with saturated NaCl solution, and dried with anhydrous sodium sulfate and filtered. The solvent was evaporated to dryness to obtain crude product, which was purified by silica gel column to obtain yellow solid Compound 5D (170 mg, 14%). LC-MS: 298 [M$^+$+1].

Step E. Synthesis of Compound 5E

Compound 5D (170 mg, 0.57 mmol, 1.0 eq) was dissolved in DMF (20 mL), and DMF solution (10 mL) of mCPBA (492 mg, 2.9 mmol) was added at −20° C., and the reaction mixture was stirred for 5 hours at −20° C. After the reaction was complete, saturated aqueous solution of Na$_2$S$_2$O$_3$ (30 mL) was added at −20° C. The mixture was extracted with DCM (2×50 mL), and the organic layer was washed with saturated NaCl solution, and dried with anhydrous sodium sulfate and filtered. The solvent was evaporated to dryness to obtain yellow oily Compound 5E (70 mg, 37%), which was directly used in the next reaction step without purification. $^1$H-NMR (400 MHz, CDCl$_3$): δ 3.14 (3H, s), 3.85 (3H, s), 6.90-6.93 (3H, m), 7.15-7.17 (3H, m), 8.07 (1H, dd), 8.28 (1H, s), 9.05 (1H, d); LC-MS: 330 [M$^+$+1].

Step F. Synthesis of Compound 5

Compound 5E (70 mg crude, 0.22 mmol) was dissolved in DCM (10 mL), and pyridine solution (10 mL) of NCS (42 mg, 0.96 mmol) and AIBN (5.0 mg) was added. The mixture was stirred overnight at room temperature. After solvent evaporation to dryness, the crude product was purified by silica gel column to obtain Compound 5 (12 mg, 16%). $^1$H-NMR (400 MHz, CDCl$_3$): δ 3.13 (3H, s), 3.86 (3H, s), 6.82 (1H, d), 6.97 (2H, d), 7.21-7.23 (2H, m), 8.06 (1H, d), 8.24 (1H, s), 9.03 (1H, s). Purity (HPLC)>95%, LC-MS: 365 [M$^+$+1].

Example 6

Preparation of 2-(5-(3-fluoro-4-methoxyphenyl)-1H-imidazol-1-yl)-5-(methylsulfonyl)pyridine (Compound 6)

Step A and Step B were the Same as Example 1

Step C. Synthesis of Compound 6C

Compound 1B (560 mg, 4.0 mmol) was dissolved in THF (30 mL), and 3-fluoro-4-methoxybenzaldehyde (620 mg, 4.0 mmol) and Ti(OiPr)$_4$ (3.5 mL) were added, respectively. The reaction mixture was heated to reflux for 1 day. After cooled to room temperature, the reaction mixture was poured into saturated NaHCO$_3$ aqueous solution. The mixture was extracted with ethyl acetate, and the organic layer was washed with saturated NaCl solution, and dried with anhydrous sodium sulfate and filtered. The solvent was evaporated to dryness to obtain Compound 6C (1.10 g, crude), which was directly used in the next reaction step without purification.

Step D. Synthesis of Compound 6D

Compound 6C (1.10 g, 4.0 mmol) was dissolved in DME (10 mL), and the MeOH solution (25 mL) of TosMIC (1.2 g, 6.0 mmol) and $K_2CO_3$ (1.4 g, 10 mmol) was added. The mixture was heated to reflux for 1 day, and then cooled to room temperature. The reaction mixture was poured into water. The mixture was extracted with ethyl acetate, and the organic layer was washed with saturated NaCl solution, and dried with anhydrous sodium sulfate and filtered. The solvent was evaporated to dryness to obtain crude product, which was purified by silica gel column to obtain yellow solid Compound 6D (140 mg, 11%). LC-MS: 316 [$M^+$+1].

Step E. Synthesis of Compound 6E

Compound 6D (140 mg, 0.45 mmol) was dissolved in DMF (20 mL), and DMF solution (10 mL) of mCPBA (380 mg, 2.2 mmol) was added at −20° C. The reaction mixture was stirred for 5 hours at −20° C. After the reaction was complete, saturated aqueous solution of $Na_2S_2O_3$ (30 mL) was added at −20° C. The mixture was extracted with DCM (2×50 mL), and the organic layer was washed with saturated NaCl solution, and dried with anhydrous sodium sulfate and filtered. The solvent was evaporated to dryness to obtain yellow oily Compound 6E (70 mg, 37%), which was directly used in the next reaction step without purification. $^1$H-NMR (400 MHz, CDCl$_3$): δ 3.18 (3H, s), 3.96 (3H, s), 6.96-7.03 (3H, m), 7.23-7.26 (2H, m), 8.16 (1H, dd), 8.31 (1H, s), 9.08 (1H, s); LC-MS: 348 [$M^+$+1].

Step F. Synthesis of Compound 6

Compound 6E (70 mg crude, 0.20 mmol) was dissolved in DCM (10 mL), and pyridine solution (10 mL) of NCS (29 mg, 0.22 mmol) and AIBN (5.0 mg) was added. The mixture was stirred overnight at room temperature. After solvent evaporation to dryness, the crude product was purified by silica gel column to obtain Compound 6 (22 mg, 29%). $^1$H-NMR (400 MHz, CDCl$_3$): δ 3.15 (3H, s), 3.95 (3H, s), 6.85 (1H, d), 7.00-7.07 (3H, m), 8.11 (1H, dd), 8.22 (1H, s), 9.04 (1H, d). Purity (HPLC)>95%, LC-MS: 383 [$M^+$+1].

Example 7

Preparation of 2-(4-chloro-5-(pyridine-3-yl)-1H-imidazol-1-yl)-5-(methylsulfonyl)pyridine (Compound 7)

Step A and Step B were the Same as Example 1

Step C. Synthesis of Compound 7C

Compound 1B (400 mg, 3.0 mmol) was dissolved in THF (30 mL), and 3-pyridylaldehyde (306 mg, 3.0 mmol) and Ti(OiPr)$_4$ (2.5 mL) were added, respectively. The reaction mixture was heated to reflux for 1 day, after cooled to room temperature, the mixture was poured into saturated NaHCO$_3$ aqueous solution. The mixture was extracted with ethyl acetate, and the organic layer was washed with saturated NaCl solution, and dried with anhydrous sodium sulfate and filtered. The solvent was evaporated to dryness to obtain Compound 7C (797 mg, crude), which was directly used in the next reaction step without purification.

Step D. Synthesis of Compound 7D

Compound 7C (797 mg, 3.5 mmol) was dissolved in DME (10 mL), and the MeOH solution (25 mL) of TosMIC (1.02 g, 5.2 mmol) and $K_2CO_3$ (1.20 g, 8.8 mmol) was added. The mixture was heated to reflux for 2 days, and then cooled to room temperature. The reaction mixture was poured into water. The mixture was extracted with ethyl acetate, and the organic layer was washed with saturated NaCl solution, and dried with anhydrous sodium sulfate and filtered. The solvent was evaporated to dryness to obtain crude product, which was purified by silica gel column to obtain yellow solid Compound 7D (151 mg, 16%). $^1$H-NMR (400 MHz, CDCl$_3$): δ 2.46 (3H, s), 6.80 (1H, d), 7.19-7.23 (2H, m), 7.43-7.49 (2H, m), 7.97 (1H, s), 8.29-8.30 (1H, m), 8.40 (1H, s), 8.45-8.47 (1H, m); LC-MS: 269 [$M^+$+1].

Step E. Synthesis of Compound 7E

Compound 7D (151 mg, 0.56 mmol) was dissolved in DMF (20 mL), and DMF solution (10 mL) of mCPBA (485 mg, 2.8 mmol) was added at −20° C. The reaction mixture was stirred for 5 hours at −20° C. After completing the reaction, saturated aqueous solution of $Na_2S_2O_3$ (30 mL) was added at −20° C. The mixture was extracted with DCM (2×50 mL), and the organic layer was washed with saturated NaCl solution, and dried with anhydrous sodium sulfate and filtered. The solvent was evaporated to dryness to obtain yellow oily Compound 7E (94 mg, crude), which was directly used in the next reaction step without purification. LC-MS: 301 [$M^+$+1].

Step F. Synthesis of Compound 7

Compound 7E (94 mg crude, 0.31 mmol) was dissolved in DCM (10 mL), and pyridine solution (10 mL) of NCS (63 mg, 0.47 mmol) and AIBN (5.0 mg) was added. The mixture was stirred overnight at room temperature. After solvent evaporation to dryness and filtration, the crude product was purified by silica gel column to obtain Compound 7 (24 mg, 23%). $^1$H-NMR (400 MHz, CDCl$_3$): δ 3.15 (3H, s), 6.93 (1H, d), 7.40-7.43 (1H, m), 7.71 (1H, d), 8.15-8.18 (1H, m), 8.22 (1H, s), 8.51 (1H, s), 8.66 (1H, d), 9.03 (1H, d). Purity (HPLC) >95%, LC-MS: 336 [$M^+$+1].

The preparation method of Examples 8-12 are set forth below, and not intended to limit the scope of the present disclosure. The chemical structure formulas and chemical names in Example 8-12 are shown in Table 3, and the structure confirmation data are shown in Table 4.

TABLE 3

The formulas and chemical names of Examples 8-12

| Example | Formula | Chemical Name (English) | Chemical Name (Chinese) |
| --- | --- | --- | --- |
| Example 8 (Compound 8) | | 5-(4-chloro-5-phenyl-1H-imidazol-1-yl)-2-(methylsulfonyl) pyridine | 5-(4-chloro-5-phenyl-1H-imidazol-1-yl)-2-(methylsulfonyl) pyridine |
| Example 8 (Compound 8E) | | 2-(methylsulfonyl)-5-(5-phenyl-1H-imidazol-1-yl) pyridine | 2-(methylsulfonyl)-5-(5-phenyl-1H-imidazol-1-yl) pyridine |
| Example 9 (Compound 9) | | 5-(4-chloro-5-(4-methoxyphenyl)-1H-imidazol-1-yl)-2-(methylsulfonyl) pyridine | 5-(4-chloro-5-(4-methoxyphenyl)-1H-imidazol-1-yl)-2-(methylsulfonyl) pyridine |
| Example 10 (Compound 10) | | 5-(4-chloro-5-(3-fluoro-4-methoxyphenyl)-1H-imidazol-1-yl)-2-(methylsulfonyl) pyridine | 5-(4-chloro-5-(3-fluoro-4-methoxyphenyl)-1H-imidazol-1-yl)-2-(methylsulfonyl) pyridine |
| Example 11 (Compound 11) | | 5-(4-chloro-5-(pyridin-3-yl)-1H-imidazol-1-yl)-2-(methylsulfonyl) pyridine | 5-(4-chloro-5-(pyridin-3-yl)-1H-imidazol-1-yl)-2-(methylsulfonyl) pyridine |

TABLE 3-continued

The formulas and chemical names of Examples 8-12

| Example | Formula | Chemical Name (English) | Chemical Name (Chinese) |
|---|---|---|---|
| Example 12 (Compound 12) | | 5-(4-chloro-5-(4-fluorophenyl)-1H-imidazol-1-yl)-2-(methylsulfonyl) pyridine | 5-(4-chloro-5-(4-fluorophenyl)-1H-imidazol-1-yl)-2-(methylsulfonyl) pyridine |

TABLE 4

The structure confirmation data of Examples 8-12

| Compound | $R^1$ | $R^2$ | $^1$H-NMR (CDCl$_3$) δ: | LC-MS m/z [M$^+$ + 1] |
|---|---|---|---|---|
| 8 | Cl | 5-phenyl | 300 MHz: 3.26 (3H, s), 7.19-7.22 (2H, m), 7.38-7.40 (3H, m), 7.66 (1H, dd), 7.71 (1H, s), 8.11 (1H, dd), 8.58 (1H, dd) | 335 |
| 8E | H | 5-pheny | 300 MHz: .27 (3H, s), 7.12-7.15 (2H, m), 7.26 (1H, s), 7.33-7.36 (4H, m), 7.71 (1H, dd), 7.80 (1H, s), 8.12 (1H, dd) | 300 |
| 9 | Cl | 4-methoxyphenyl | 400 MHz:. 3.26 (3H, s), 3.83 (3H, s), 6.90 (2H, d), 7.11 (2H, d), 7.63-7.66 (1H, m), 7.68 (1H, s), 8.10 (1H, d), 8.56 (1H, d) | 365 |
| 10 | Cl | 3-fluoro-4-methoxyphenyl | 400 MHz: 3.27 (3H, s), 3.91 (3H, s), 6.84 (1H, d), 6.93-7.02 (2H, m), 7.66-7.68 (2H, m), 8.12 (1H, d), 8.56 (1H, d). | 383 |
| 11 | Cl | 3-pyridyl | 400 MHz: 3.27 (3H, s), 7.35-7.38 (2H, m), 7.57-7.60 (1H, m), 7.67-7.74 (1H, m), 8.14 (1H, d), 8.46 (1H, d), 8.58 (1H, d), 8.62 (1H, d) | 336 |
| 12 | Cl | 4-fluorophenyl | 400 MHz: 3.26 (3H, s), 7.08-7.12 (2H, m), 7.17-7.21 (2H, m), 7.65 (1H, dd), 7.70 (1H, s), 8.12 (1H, d), 8.56 (1H, d) | 353 |

The synthetic route of Examples 8-12 is shown as below:

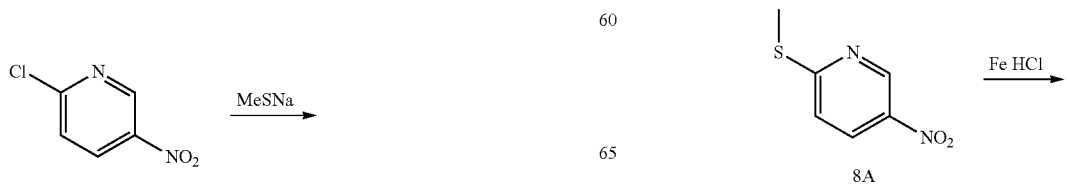

37

-continued

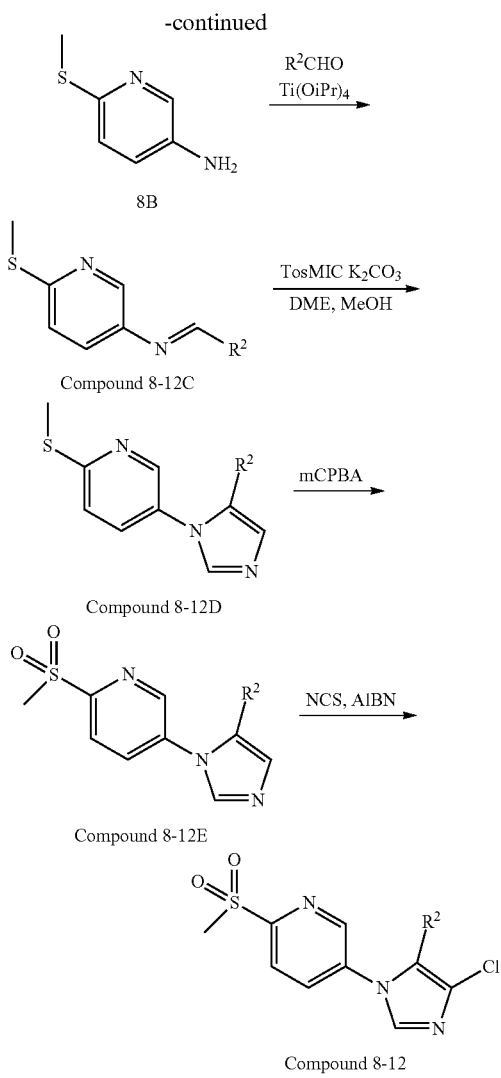

Example 8

Preparation of Compound 5-(4-chloro-5-phenyl-1H-imidazol-1-yl)-2-(methylsulfonyl)pyridine (Compound 8)

Step A. Preparation of Compound 2-(methylthio)-5-nitropyridine (Compound 8 A)

The methanol solution of methyl sodium sulfide (6 g, 86 mmol) was added portionwise at 0° C. into the methanol solution of 2-chloro-5-nitropyridine (2 g, 13 mmol). Then, the reaction mixture was heated to room temperature and stirred for 14 hours. The reaction mixture was poured into 20 mL water, and extracted with ethyl acetate 20 mL for three times. The organic phases were combined, dried with anhydrous sodium sulfate, filtered and concentrated. The residual was recrystallized in diethyl ether to yield yellow solid 2-(methylthio)-5-nitropyridine (2 g, 12 mmol). $^1$H-NMR (300 MHz, CDCl$_3$): δ 2.64 (3H, s), 7.28-7.32 (1H, m), 9.24 (1H, dd), 9.26 (1H, d); LC-MS m/z: 171 [M$^+$+1]; purity (HPLC) >95%.

38

Step B. Preparation of Compound 2-(methylthio)-5-aminopyridine (Compound 8 B)

Iron powder (3 g), water (20 mL) and concentrated hydrochloric acid (3 mL) were mixed, and 2-(methylthio)-5-nitropyridine (2 g, 12 mmol) was added portionwise. After reflux reaction for 2 hours, the reaction mixture was basified with 1N sodium hydroxide and extracted with 20 mL ethyl acetate for three times. The combined organic phase was dried with anhydrous sodium sulfate, filtered and concentrated to yield the target compound (1.54 g, 11 mmol).

Step C. Preparation of compound N-benzal-6-(methylthio)pyridine-3-amine (Compound 8C)

2-(methylthio)-5-aminopyridine (1 g, 7 mmol), benzaldehyde (0.76 g, 7 mmol), tetraisopropyl titanate (3 mL) and tetrahydrofuran (25 mL) were mixed and stirred to react at 70° C. for 24 hours. Saturated sodium carbonate solution was added into the reaction mixture, and the mixture was extracted with ethyl acetate for three times. The combined organic phase was dried with anhydrous sodium sulfate, filtered and concentrated to yield the residual (1.72 g), which was directly used in the next reaction step without purification.

Step D. Preparation of Compound 2-(methylthio)-5-(5-phenyl-1H-imidazol-1-yl)pyridine (Compound 8 D)

N-benzal-6-(methylthio)pyridine-3-amine (1.72 g, resulting from the previous step), tosylmethyl isocyanide (2.2 g, 11 mmol), sodium carbonate (2.1 g, 16 mmol), methanol (50 mL) and ethylene glycol dimethyl ether (20 mL) were mixed, and stirred to react at 70° C. for 3 hours. Water (100 mL) was added into the reaction mixture, and the mixture was extracted with ethyl acetate for three times. The combined organic phase was dried with anhydrous sodium sulfate, filtered and concentrated. The residual was purified by column chromatography (petroleum ether/ethyl acetate=10/1) to yield white solid target compound (500 mg, 2 mmol).

Step E. Preparation of Compound 2-(methylsulfonyl)-5-(5-phenyl-1H-imidazol-1-yl)pyridine (Compound 8 E)

2-(methylthio)-5-(5-phenyl-1H-imidazol-1-yl)pyridine (250 mg, 0.94 mmol) was dissolved in 5 mL dichloromethane, and dichloromethane (5 mL) of m-chloroperoxybenzoic acid (742 mg, 4.3 mmol) was added dropwise at 0° C. The reaction mixture was stirred to react at room temperature for 1.5 hours. The reaction mixture was diluted with dichloromethane (20 mL) and washed 2 times with saturated Na$_2$S$_2$O$_3$ aqueous solution. The organic phase was dried with anhydrous sodium sulfate, filtered and concentrated. The crude product was purified by column chromatography (petroleum ether/ethyl acetate=20:1) to yield white solid target compound (100 mg, 0.33 mmol). $^1$H-NMR (300 MHz, CDCl$_3$): δ 3.27 (3H, s), 7.12-7.15 (2H, m), 7.26 (1H, s), 7.33-7.36 (4H, m), 7.71 (1H, dd), 7.80 (1H, s), 8.12 (1H, dd); LC-MS m/z: 300 [M$^+$+1]; purity (HPLC)>95%.

Step. F Preparation of Compound 5-(4-chloro-5-phenyl-1H-imidazol-1-yl)-2-(methylsulfonyl)pyridine (Compound 8)

2-(methylsulfonyl)-5-(5-phenyl-1H-imidazol-1-yl)pyridine (83 mg, 0.28 mmol), N-chlorosuccinimide (39 mg, 0.29 mmol), azobisisobutyronitrile (2 mg) and tetrahydrofuran (10 mL) were added into a 25 mL round bottom flask, and stirred to conduct reflux reaction for 18 hours. After the reaction, the solution was concentrated under reduced pressure, and the crude product was purified by column chromatography (petroleum ether/ethyl acetate=20:1) to yield white solid target compound (56 mg, 0.17 mmol). $^1$H-NMR (300 MHz, CDCl$_3$): δ 3.26 (3H, s), 7.19-7.22 (2H, m), 7.38-7.40 (3H, m), 7.66 (1H, dd), 7.71 (1H, s), 8.11 (1H, dd), 8.58 (1H, dd); LC-MS m/z: 335 [M$^+$+1]; purity (HPLC)>95%.

Example 9

Preparation of Compound 5-(4-chloro-5-(4-methoxyphenyl)-1H-imidazol-1-yl)-2-(methylsulfonyl)pyridine (Compound 9)

Step A and Step B were the Same as Example 8

Step C. Synthesis of Compound 9C

Compound 8B (560 mg, 4.0 mmol) was dissolved in THF (30 mL), and then 4-methoxybenzaldehyde (550 mg, 4.0 mmol) and Ti(OiPr)$_4$ (3.6 mL) were added, respectively. The reaction mixture was heated to reflux for 2 days, and then cooled to room temperature. The reaction mixture was poured into saturated NaHCO$_3$ solution. The mixture was extracted with ethyl acetate, and the organic layer was washed with saturated NaCl solution, dried with anhydrous sodium sulfate. The filtered and concentrated product 9C (1.10 g, crude) was directly used in the next reaction step without purification.

Step D. Synthesis of Compound 9D

Compound 9C (1.10 g, 3.5 mmol) was dissolved in DMF (10 mL), and the methanol solution (25 mL) of TosMIC (1.02 g, 5.2 mmol) and K$_2$CO$_3$ (1.40 g, 10 mmol) was added. The reaction mixture was heated to reflux for 2 days, and then cooled to room temperature. The reaction mixture was poured into water and extracted with ethyl acetate. The organic layer was washed with saturated NaCl solution, dried with anhydrous sodium sulfate and filtered. The solvent was evaporated to dryness to yield crude product, which was purified by silica gel column to yield yellow solid compound 9D (400 mg, 33%). LC-MS: 298 [M$^+$+1].

Step E. Synthesis of Compound 9E

Compound 9D (400 mg, 1.40 mmol) was dissolved in DMF (20 mL), and DMF solution (10 mL) of mCPBA (1.2 g, 6.7 mmol) was added at −20° C., and the reaction mixture was stirred for 5 hours at −20° C. After the reaction is complete, Na$_2$S$_2$O$_3$ saturated aqueous solution (30 mL) was added at −20° C. The mixture was extracted with DCM (2×50 mL), and the organic layer was washed with saturated NaCl solution, dried with anhydrous sodium sulfate and filtered. The solvent was evaporated to dryness to yield yellow oily compound 9E (93 mg, 21%), which was directly used in the next reaction step without purification. LC-MS: 330 [M$^+$+1].

Step F. Synthesis of Compound 9

The crude product of Compound 9E (93 mg, 0.28 mmol) was dissolved in DCM (10 mL), and pyridine solution (10 mL) of NCS (41 mg, 0.31 mmol) and AIBN (5.0 mg) was added. The mixture was stirred overnight at room temperature. After solvent evaporation to dryness, the crude product was purified by silica gel column to yield Compound 9 (30 mg, 29%). $^1$H-NMR (400 MHz, CDCl$_3$): δ 3.26 (3H, s), 3.83 (3H, s), 6.90 (2H, d), 7.11 (2H, d), 7.63-7.66 (1H, m), 7.68 (1H, s), 8.10 (1H, d), 8.56 (1H, d); purity (HPLC)>95%, LC-MS: 365 [M$^+$+1].

Example 10

Preparation of Compound 5-(4-chloro-5-(3-fluoro-4-methoxyphenyl)-1H-imidazol-1-yl)-2-(methylsulfonyl)pyridine (Compound 10)

Step A and Step B were the Same as Example 8

Step C. Synthesis of Compound 10C

Compound 8B (420 mg, 3.0 mmol) was dissolved in THF (30 mL), and 3-fluoro-4-methoxybenzaldehyde (460 mg, 3.0 mmol) and Ti(OiPr)$_4$ (2.6 mL) were added, respectively. The reaction mixture was heated to reflux for 1 day, and then cooled to room temperature. The reaction mixture was poured into saturated NaHCO$_3$ solution. The mixture was extracted with ethyl acetate, and the organic layer was washed with saturated NaCl solution, dried with anhydrous sodium sulfate and filtered. The solvent was evaporated to dryness to yield Compound 10C (0.80, crude), which was directly used in the next reaction step without purification.

Step D. Synthesis of Compound 10D

Compound 10C (0.72 g, 2.6 mmol) was dissolved in DME (10 mL), and the MeOH solution (25 mL) of TosMIC (0.76 g, 3.9 mmol) and K$_2$CO$_3$ (0.9 g, 6.5 mmol) was added. The reaction mixture was heated to reflux for 1 day, and then cooled to room temperature. The reaction mixture was poured into water and extracted with ethyl acetate. The organic layer was washed with saturated NaCl solution, dried with anhydrous sodium sulfate and filtered. The solvent was evaporated to dryness to yield crude product, which was purified by silica gel column to yield yellow solid compound 10D (580 mg, 71%). $^1$H-NMR (400 MHz, CDCl$_3$): δ 2.58 (3H, s), 3.88 (3H, s), 6.85-6.90 (3H, m), 7.20-7.24 (3H, m), 7.65 (1H, m), 8.36 (1H, d); LC-MS: 316 [M$^+$+1].

Step E. Synthesis of Compound 10E

Compound 10D (580 mg, 1.90 mmol) was dissolved in DMF (20 mL), and DMF solution (10 mL) of mCPBA (1.6 g, 6.3 mmol) was added at −20° C., and the reaction mixture was stirred for 5 hours at −20° C. After the reaction is complete, Na$_2$S$_2$O$_3$ saturated aqueous solution (30 mL) was added at −20° C. The mixture was extracted with DCM (2×50 mL), and the organic layer was washed with saturated NaCl solution, dried with anhydrous sodium sulfate and filtered. The solvent was evaporated to dryness to yield yellow oily compound 10E (140 mg, 22%), which was directly used in the next reaction step without purification. LC-MS: 348 [M$^+$+1].

Step F. Synthesis of Compound 10

The crude product of compound 10D (140 mg, 0.40 mmol) was dissolved in DCM (10 mL), and pyridine solution (10 mL) of NCS (60 mg, 0.66 mmol) and AIBN (5.0 mg) was added. The mixture was stirred overnight at room temperature. After solvent evaporation to dryness, the crude product was purified by silica gel column to yield Compound 10 (75 mg, 50%). $^1$H-NMR (400 MHz, CDCl$_3$): δ 3.27 (3H, s), 3.91 (3H, s), 6.84 (1H, d), 6.93-7.02 (2H, m), 7.66-7.68 (2H, m), 8.12 (1H, d), 8.56 (1H, d); purity (HPLC)>95%, LC-MS: 383 [M$^+$+1].

Example 11

Preparation of Compound 5-(4-chloro-5-(pyridine-3-yl)-1H-imidazol-1-yl)-2-(methylsulfonyl)pyridine (Compound 11)

Step A and Step B were the Same as Example 8

Step C. Synthesis of Compound 11C

Compound 8B (420 mg, 3.0 mmol) was dissolved in THF (30 mL), and 3-pyridylaldehyde (320 mg, 3.0 mmol) and Ti(OiPr)$_4$ (2.2 mL) were added, respectively. The reaction mixture was heated to reflux for 1 day, and then cooled to room temperature. The reaction mixture was poured into saturated NaHCO$_3$ aqueous solution. The mixture was extracted with ethyl acetate, and the organic layer was washed with saturated NaCl solution, dried with anhydrous sodium sulfate and filtered. The solvent was evaporated to dryness to yield Compound 11C (0.73, crude), which was directly used in the next reaction step without purification.

Step D. Synthesis of Compound 11D

Compound 11C (0.73 g, 3.0 mmol) was dissolved in DME (10 mL), and the MeOH solution (25 mL) of TosMIC (0.88 g, 4.5 mmol) and K$_2$CO$_3$ (1.0 g, 7.5 mmol) was added. The reaction mixture was heated to reflux for 1 day, and then cooled to room temperature. The reaction mixture was poured into water and extracted with ethyl acetate. The organic layer was washed with saturated NaCl solution, dried with anhydrous sodium sulfate and filtered. The solvent was evaporated to dryness to yield crude product, which was purified by silica gel column to yield yellow solid compound 11D (570 mg, 71%). $^1$H-NMR (400 MHz, CDCl$_3$): δ 2.51 (3H, s), 7.13-7.20 (4H, m), 7.34-7.37 (1H, m), 7.67 (1H, s), 8.30 (1H, d), 8.41 (1H, d), 8.45 (1H, dd); LC-MS: 269 [M$^+$+1].

Step E. Synthesis of Compound 11E

Compound 11D (570 mg, 2.1 mmol) was dissolved in DMF (20 mL), and DMF solution (10 mL) of mCPBA (1.8 g, 10 mmol) was added at −20° C., and the reaction mixture was stirred for 5 hours at −20° C. After the reaction is complete, Na$_2$S$_2$O$_3$ saturated aqueous solution (30 mL) was added at −20° C. The mixture was extracted with DCM (2×50 mL), and the organic layer was washed with saturated NaCl solution, dried with anhydrous sodium sulfate and filtered. The solvent was evaporated to dryness to yield yellow oily compound 11E (550 mg, crude), which was directly used in the next reaction step without purification. LC-MS: 301 [M$^+$+1].

Step F. Synthesis of Compound 11

The crude product of compound 11E (550 mg, 1.8 mmol) was dissolved in DCM (10 mL), and pyridine solution (10 mL) of NCS (270 mg, 2.0 mmol) and AIBN (5.0 mg) was added. The mixture was stirred overnight at room temperature. After solvent evaporation to dryness, the crude product was purified by silica gel column to yield Compound 11 (69 mg, 33%). $^1$H-NMR (400 MHz, CDCl$_3$): δ 3.27 (3H, s), 7.35-7.38 (2H, m), 7.57-7.60 (1H, m), 7.67-7.74 (1H, m), 8.14 (1H, d), 8.46 (1H, d), 8.58 (1H, d), 8.62 (1H, d). Purity (HPLC)>95%, LC-MS: 336 [M$^+$+1].

Example 12

Preparation of Compound 5-(4-chloro-5-(4-fluorophenyl)-1H-imidazol-1-yl)-2-(methylsulfonyl)pyridine (Compound 12)

Step A and Step B were the Same as Example 8

Step C. Synthesis of Compound 12C

Compound 8B (420 mg, 3.0 mmol) was dissolved in THF (30 mL), and then 4-methoxybenzaldehyde (370 mg, 3.0 mmol) and Ti(OiPr)$_4$ (3.6 mL) were added, respectively. The reaction mixture was heated to reflux for 1 day, and then cooled to room temperature. The reaction mixture was poured into saturated NaHCO$_3$ solution. The mixture was extracted with ethyl acetate, and the organic layer was washed with saturated NaCl solution, dried with anhydrous sodium sulfate. The filtered and concentrated product 12C (0.80 g crude) was directly used in the next reaction step without purification.

Step D. Synthesis of Compound 12D

Compound 12C (800 mg, 3.2 mmol) was dissolved in DMF (10 mL), and MeOH solution (25 mL) of TosMIC (0.95 g, 4.9 mmol) and K$_2$CO$_3$ (1.1 g, 8.1 mmol). The reaction mixture was heated to reflux for 1 day, and then cooled to room temperature. The reaction mixture was poured into water and extracted with ethyl acetate. The organic layer was washed with saturated NaCl solution, dried with anhydrous sodium sulfate and filtered. The solvent was evaporated to dryness to yield crude product, which was purified by silica gel column to yield yellow solid compound 12D (745 mg, 80%). $^1$H-NMR (400 MHz, CDCl$_3$): δ 2.61 (3H, s), 7.03-7.05 (2H, m), 7.13-7.15 (2H, m), 7.22-7.27 (3H, m), 7.70 (1H, s), 8.38 (1H, d); LC-MS: 286 [M$^+$+1].

Step E. Synthesis of Compound 12E

Compound 12D (740 mg, 2.6 mmol) was dissolved in DMF (20 mL), and DMF solution (10 mL) of mCPBA (2.3 g, 13 mmol) was added at −20° C., and the reaction mixture was stirred for 5 hours at −20° C. After completing the reaction, Na$_2$S$_2$O$_3$ saturated aqueous solution (30 mL) was added at −20° C. The mixture was extracted with DCM (2×50 mL), and the organic layer was washed with saturated NaCl solution, dried with anhydrous sodium sulfate and filtered. The solvent was evaporated to dryness to yield yellow oily compound 12E (140 mg, 17%), which was directly used in the next reaction step without purification. LC-MS: 318 [M$^+$+1].

Step F. Synthesis of Compound 12

Compound 12E (140 mg, 0.44 mmol) was dissolved in DCM (10 mL), and pyridine solution (10 mL) of NCS (80 mg, 0.66 mmol) and AIBN (10 mg) was added. The mixture was stirred overnight at room temperature. After solvent evaporation to dryness, the crude product was purified by silica gel column to yield Compound 12 (32 mg, 20%). $^1$H-NMR (400 MHz, CDCl$_3$): δ 3.26 (3H, s), 7.08-7.12 (2H, m), 7.17-7.21 (2H, m), 7.65 (1H, dd), 7.70 (1H, s), 8.12 (1H, d), 8.56 (1H, d); purity (HPLC)>95%; LC-MS: 353 [M$^+$+1].

The following compounds are also encompassed within the protection scope of the present disclosure. They can be prepared according to the synthesis method of Example 1 described above, but this should not be construed as an limitation, as they can be also prepared by other synthetic methods. Their formulas and chemical names are shown in Table 5:

TABLE 5

| Compounds 13-53 | | | |
|---|---|---|---|
| Compound | Formula | Chemical name (English) | Chemical name (Chinese) |
| 13 | | 2-(4-chloro-5-(3-chloro-4-methoxyphenyl)-1H-imidazol-1-yl)-5-(methylsulfonyl) pyridine | 2-(4-chloro-5-(3-chloro-4-methoxyphenyl)-1H-imidazol-1-yl)-5-(methylsulfonyl) pyridine |
| 14 | | 2-(4-chloro-5-(3-fluorophenyl)-1H-imidazol-1-yl)-5-(methylsulfonyl) pyridine | 2-(4-chloro-5-(3-fluorophenyl)-1H-imidazol-1-yl)-5-(methylsulfonyl) pyridine |
| 15 | | 2-(4-chloro-5-(3-fluoro-4-methylphenyl)-1H-imidazol-1-yl)-5-(methylsulfonyl) pyridine | 2-(4-chloro-5-(3-fluoro-4-methylphenyl)-1H-imidazol-1-yl)-5-(methylsulfonyl) pyridine |
| 16 | | 2-(4-chloro-5-(2-fluorophenyl)-1H-imidazol-1-yl)-5-(methylsulfonyl) pyridine | 2-(4-chloro-5-(2-fluorophenyl)-1H-imidazol-1-yl)-5-(methylsulfonyl) pyridine |

TABLE 5-continued

Compounds 13-53

| Compound | Formula | Chemical name (English) | Chemical name (Chinese) |
|---|---|---|---|
| 17 | | 2-(5-(2,4-difluorophenyl)-1H-imidazol-1-yl)-5-(methylsulfonyl) pyridine | 2-(5-(2,4-difluorophenyl)-1H-imidazol-1-yl)-5-(methylsulfonyl) pyridine |
| 18 | | 2-(5-(2,4-difluorophenyl)-1H-imidazol-1-yl)-5-(methylsulfonyl) pyridine | 2-(5-(2,4-difluorophenyl)-1H-imidazol-1-yl)-5-(methylsulfonyl) pyridine |
| 19 | | 2-(5-(3-fluorophenyl)-1H-imidazol-1-yl)-5-(methylsulfonyl) pyridine | 2-(5-(3-fluorophenyl)-1H-imidazol-1-yl)-5-(methylsulfonyl) pyridine |
| 20 | | 2-(5-(3-fluoro-4-methylphenyl)-1H-imidazol-1-yl)-5-(methylsulfonyl) pyridine | 2-(5-(3-fluoro-4-methylphenyl)-1H-imidazol-1-yl)-5-(methylsulfonyl) pyridine |
| 21 | | 2-(5-(2-fluorophenyl)-1H-imidazol-1-yl)-5-(methylsulfonyl) pyridine | 2-(5-(2-fluorophenyl)-1H-imidazol-1-yl)-5-(methylsulfonyl) pyridine |

TABLE 5-continued

Compounds 13-53

| Compound | Formula | Chemical name (English) | Chemical name (Chinese) |
|---|---|---|---|
| 22 | | 5-(methylsulfonyl)-2-(5-(4-(trifluoromethoxy)phenyl)-1H-imidazol-1-yl) pyridine | 5-(methylsulfonyl)-2-(5-(4-(trifluoromethoxy)phenyl)-1H-imidazol-1-yl) pyridine |
| 23 | | 4-methyl-3-(1-(5-(methylsulfonyl)pyridin-2-yl)-1H-imidazol-5-yl) pyridine | 4-methyl-3-(1-(5-(methylsulfonyl)pyridin-2-yl)-1H-imidazol-5-yl) pyridine |
| 24 | | 2-(5-(2-fluoro-4-methoxyphenyl)-1H-imidazol-1-yl)-5-(methylsulfonyl) pyridine | 2-(5-(2-fluoro-4-methoxyphenyl)-1H-imidazol-1-yl)-5-(methylsulfonyl) pyridine |
| 25 | | 2-(5-(3-chloro-4-methylphenyl)-1H-imidazol-1-yl)-5-(methylsulfonyl) pyridine | 2-(5-(3-chloro-4-methylphenyl)-1H-imidazol-1-yl)-5-(methylsulfonyl) pyridine |

TABLE 5-continued

Compounds 13-53

| Compound | Formula | Chemical name (English) | Chemical name (Chinese) |
|---|---|---|---|
| 26 | | 2-(5-(3-methoxy-4-methylphenyl)-1H-imidazol-1-yl)-5-(methylsulfonyl) pyridine | 2-(5-(3-methoxy-4-methylphenyl)-1H-imidazol-1-yl)-5-(methylsulfonyl) pyridine |
| 27 | | 2-(5-(4-chlorophenyl)-1H-imidazol-1-yl)-5-(methylsulfonyl) pyridine | 2-(5-(4-chlorophenyl)-1H-imidazol-1-yl)-5-(methylsulfonyl) pyridine |
| 28 | | 4-chloro-3-(1-(5-(methylsulfonyl)pyridin-2-yl)-1H-imidazol-5-yl) pyridine | 4-chloro-3-(1-(5-(methylsulfonyl)pyridin-2-yl)-1H-imidazol-5-yl) pyridine |
| 29 | | 2,4-dichloro-3-(1-(5-(methylsulfonyl)pyridin-2-yl)-1H-imidazol-5-yl) pyridine | 2,4-dichloro-3-(1-(5-(methylsulfonyl)pyridin-2-yl)-1H-imidazol-5-yl) pyridine |
| 30 | | 2-(5-(2-chloro-4-methoxypyridin-3-yl)-1H-imidazol-1-yl)-5-(methylsulfonyl) pyridine | 2-(5-(2-chloro-4-methoxypyridin-3-yl)-1H-imidazol-1-yl)-5-(methylsulfonyl) pyridine |

TABLE 5-continued

Compounds 13-53

| Compound | Formula | Chemical name (English) | Chemical name (Chinese) |
|---|---|---|---|
| 31 | | 3,4-dichloro-5-(1-(5-(methylsulfonyl)pyridin-2-yl)-1H-imidazol-5-yl) pyridine | 3,4-dichloro-5-(1-(5-(methylsulfonyl)pyridin-2-yl)-1H-imidazol-5-yl) pyridine |
| 32 | | 5-(methylsulfonyl)-2-(5-(4-propoxyphenyl)-1H-imidazol-1-yl) pyridine | 5-(methylsulfonyl)-2-(5-(4-propoxyphenyl)-1H-imidazol-1-yl) pyridine |
| 33 | | 2-(5-(3,5-diethoxyphenyl)-1H-imidazol-1-yl)-5-(methylsulfonyl) pyridine | 2-(5-(3,5-diethoxyphenyl)-1H-imidazol-1-yl)-5-(methylsulfonyl) pyridine |
| 34 | | 2-(5-(4-ethoxyphenyl)-1H-imidazol-1-yl)-5-(methylsulfonyl) pyridine | 2-(5-(4-ethoxyphenyl)-1H-imidazol-1-yl)-5-(methylsulfonyl) pyridine |
| 35 | | 5-(methylsulfonyl)-2-(5-(4-nitrophenyl)-1H-imidazol-1-yl) pyridine | 5-(methylsulfonyl)-2-(5-(4-nitrophenyl)-1H-imidazol-1-yl) pyridine |

TABLE 5-continued

Compounds 13-53

| Compound | Formula | Chemical name (English) | Chemical name (Chinese) |
|---|---|---|---|
| 36 | | 2-(5-(4-(methylsulfinyl)phenyl)-1H-imidazol-1-yl)-5-(methylsulfonyl) pyridine | 2-(5-(4-(methylsulfinyl)phenyl)-1H-imidazol-1-yl)-5-(methylsulfonyl) pyridine |
| 37 | | 2-(5-(4-(ethylsulfinyl)phenyl)-1H-imidazol-1-yl)-5-(methylsulfonyl) pyridine | 2-(5-(4-(ethylsulfinyl)phenyl)-1H-imidazol-1-yl)-5-(methylsulfonyl) pyridine |
| 38 | | N,N-dimethyl-4-(1-(5-(methylsulfonyl)pyridin-2-yl)-1H-imidazol-5-yl) benzenamine | N,N-dimethyl-4-(1-(5-(methylsulfonyl)pyridin-2-yl)-1H-imidazol-5-yl) benzenamine |
| 39 | | 2-(5-(4-fluorophenyl)-4-methyl-1H-imidazol-1-yl)-5-(methylsulfonyl) pyridine | 2-(5-(4-fluorophenyl)-4-methyl-1H-imidazol-1-yl)-5-(methylsulfonyl) pyridine |

TABLE 5-continued

Compounds 13-53

| Compound | Formula | Chemical name (English) | Chemical name (Chinese) |
|---|---|---|---|
| 40 | | 2-(4-chloro-5-(2,4-difluorophenyl)-1H-imidazol-1-yl)-5-(methylsulfonyl)pyridine | 2-(4-chloro-5-(2,4-difluorophenyl)-1H-imidazol-1-yl)-5-(methylsulfonyl)pyridine |
| 41 | | 2-(4-chloro-5-(2-chloro-4-methoxypyridin-3-yl)-1H-imidazol-1-yl)-5-(methylsulfonyl)pyridine | 2-(4-chloro-5-(2-chloro-4-methoxypyridin-3-yl)-1H-imidazol-1-yl)-5-(methylsulfonyl)pyridine |
| 42 | | 3,4-dichloro-5-(4-chloro-1-(5-(methylsulfonyl)pyridin-2-yl)-1H-imidazol-5-yl) pyridine | 3,4-dichloro-5-(4-chloro-1-(5-(methylsulfonyl)pyridin-2-yl)-1H-imidazol-5-yl) pyridine |
| 43 | | 2-(4-chloro-5-(4-propoxyphenyl)-1H-imidazol-1-yl)-5-(methylsulfonyl) pyridine | 2-(4-chloro-5-(4-propoxyphenyl)-1H-imidazol-1-yl)-5-(methylsulfonyl) pyridine |
| 44 | | 2-(4-chloro-5-(3,5-diethoxyphenyl)-1H-imidazol-1-yl)-5-(methylsulfonyl) pyridine | 2-(4-chloro-5-(3,5-diethoxyphenyl)-1H-imidazol-1-yl)-5-(methylsulfonyl) pyridine |

TABLE 5-continued

Compounds 13-53

| Compound | Formula | Chemical name (English) | Chemical name (Chinese) |
|---|---|---|---|
| 45 | 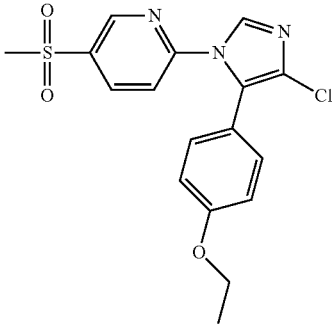 [SMILES: CCOc1ccc(-c2c(Cl)ncn2-c2ccc(S(C)(=O)=O)cn2)cc1] | 2-(4-chloro-5-(4-ethoxyphenyl)-1H-imidazol-1-yl)-5-(methylsulfonyl) pyridine | 2-(4-chloro-5-(4-ethoxyphenyl)-1H-imidazol-1-yl)-5-(methylsulfonyl) pyridine |
| 46 | 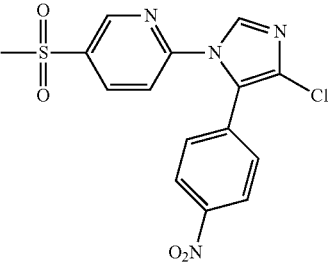 [SMILES: CS(=O)(=O)c1ccc(-n2cnc(Cl)c2-c2ccc([N+](=O)[O-])cc2)nc1] | 2-(4-chloro-5-(4-nitrophenyl)-1H-imidazol-1-yl)-5-(methylsulfonyl) pyridine | 2-(4-chloro-5-(4-nitrophenyl)-1H-imidazol-1-yl)-5-(methylsulfonyl) pyridine |
| 47 | 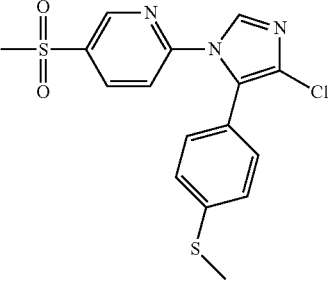 [SMILES: CSc1ccc(-c2c(Cl)ncn2-c2ccc(S(C)(=O)=O)cn2)cc1] | 2-(4-chloro-5-(4-(methylthio)phenyl)-1H-imidazol-1-yl)-5-(methylsulfonyl) pyridine | 2-(4-chloro-5-(4-(methylthio)phenyl)-1H-imidazol-1-yl)-5-(methylsulfonyl) pyridine |
| 48 | 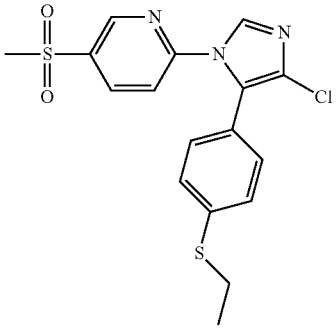 [SMILES: CCSc1ccc(-c2c(Cl)ncn2-c2ccc(S(C)(=O)=O)cn2)cc1] | 2-(4-chloro-5-(4-(ethylthio)phenyl)-1H-imidazol-1-yl)-5-(methylsulfonyl) pyridine | 2-(4-chloro-5-(4-(ethylthio)phenyl)-1H-imidazol-1-yl)-5-(methylsulfonyl) pyridine |
| 49 | 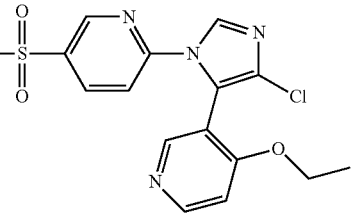 | 2-(4-chloro-5-(4-ethoxypyridin-3-yl)-1H-imidazol-1-yl)-5-(methylsulfonyl) pyridine | 2-(4-chloro-5-(4-ethoxypyridin-3-yl)-1H-imidazol-1-yl)-5-(methylsulfonyl) pyridine |

TABLE 5-continued

Compounds 13-53

| Compound | Formula | Chemical name (English) | Chemical name (Chinese) |
|---|---|---|---|
| 50 | 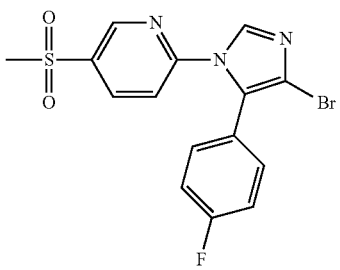 [SMILES: CS(=O)(=O)c1ccc(-n2cnc(Br)c2-c2ccc(F)cc2)nc1] | 2-(4-bromo-5-(4-fluorophenyl)-1H-imidazol-1-yl)-5-(methylsulfonyl) pyridine | 2-(4-bromo-5-(4-fluorophenyl)-1H-imidazol-1-yl)-5-(methylsulfonyl) pyridine |
| 51 | 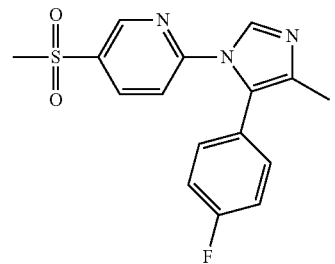 | 2-(5-(4-fluorophenyl)-4-methyl-1H-imidazol-1-yl)-5-(methylsulfonyl) pyridine | 2-(5-(4-fluorophenyl)-4-methyl-1H-imidazol-1-yl)-5-(methylsulfonyl) pyridine |
| 52 | 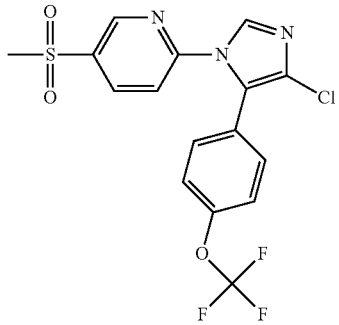 [SMILES: CS(=O)(=O)c1ccc(-n2cnc(Cl)c2-c2ccc(OC(F)(F)F)cc2)nc1] | 2-(4-chloro-5-(4-(trifluoromethoxy)phenyl)-1H-imidazol-1-yl)-5-(methylsulfonyl) pyridine | 2-(4-chloro-5-(4-(trifluoromethoxy)phenyl)-1H-imidazol-1-yl)-5-(methylsulfonyl) pyridine |
| 53 | 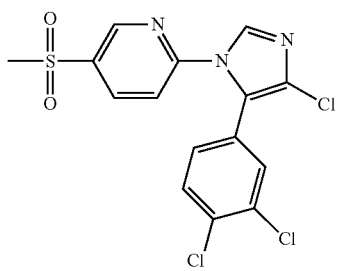 [SMILES: CS(=O)(=O)c1ccc(-n2cnc(Cl)c2-c2ccc(Cl)c(Cl)c2)nc1] | 2-(4-chloro-5-(3,4-dichlorophenyl)-1H-imidazol-1-yl)-5-(methylsulfonyl)pyridine | 2-(4-chloro-5-(3,4-dichlorophenyl)-1H-imidazol-1-yl)-5-(methylsulfonyl)pyridine |

The following compounds are also encompassed within the protection scope of the present disclosure. They can be prepared according to the synthesis methods of Example 8 described above, but this should not be construed as an limitation, as they can be also prepared by other synthetic methods. Their formulas and chemical names are shown in Table 6:

TABLE 6

Compounds 54-99

| Compound | Formula | Chemical name (English) | Chemical name (Chinese) |
|---|---|---|---|
| 54 | | 5-(4-chloro-5-(3-fluorophenyl)-1H-imidazol-1-yl)-2-(methylsulfonyl) pyridine | 5-(4-chloro-5-(3-fluorophenyl)-1H-imidazol-1-yl)-2-(methylsulfonyl) pyridine |
| 55 | | 5-(4-chloro-5-(3-fluoro-4-methylphenyl)-1H-imidazol-1-yl)-2-(methylsulfonyl) pyridine | 5-(4-chloro-5-(3-fluoro-4-methylphenyl)-1H-imidazol-1-yl)-2-(methylsulfonyl) pyridine |
| 56 | | 5-(4-chloro-5-(2-fluorophenyl)-1H-imidazol-1-yl)-2-(methylsulfonyl) pyridine | 5-(4-chloro-5-(2-fluorophenyl)-1H-imidazol-1-yl)-2-(methylsulfonyl) pyridine |
| 57 | | 5-(4-chloro-5-(4-(trifluoromethoxy)phenyl)-1H-imidazol-1-yl)-2-(methylsulfonyl) pyridine | 5-(4-chloro-5-(4-(trifluoromethoxy)phenyl)-1H-imidazol-1-yl)-2-(methylsulfonyl) pyridine |
| 58 | | 5-(5-(4-fluorophenyl)-1H-imidazol-1-yl)-2-(methylsulfonyl) pyridine | 5-(5-(4-fluorophenyl)-1H-imidazol-1-yl)-2-(methylsulfonyl) pyridine |

TABLE 6-continued

| | | Chemical name | Chemical name |
|---|---|---|---|
| Compound | Formula | (English) | (Chinese) |
| 59 | | 2-(methylsulfonyl)-5-(5-p-tolyl-1H-imidazol-1-yl) pyridine | 2-(methylsulfonyl)-5-(5-p-tolyl-1H-imidazol-1-yl) pyridine |
| 60 | | 5-(5-(2,4-difluorophenyl)-1H-imidazol-1-yl)-2-(methylsulfonyl)pyridine | 5-(5-(2,4-difluorophenyl)-1H-imidazol-1-yl)-2-(methylsulfonyl)pyridine |
| 61 | | 5-(5-(2,4-dichlorophenyl)-1H-imidazol-1-yl)-2-(methylsulfonyl) pyridine | 5-(5-(2,4-dichlorophenyl)-1H-imidazol-1-yl)-2-(methylsulfonyl) pyridine |
| 62 | | 5-(5-(4-methoxyphenyl)-1H-imidazol-1-yl)-2-(methylsulfonyl) pyridine | 5-(5-(4-methoxyphenyl)-1H-imidazol-1-yl)-2-(methylsulfonyl) pyridine |
| 63 | | 5-(5-(3-fluoro-4-methoxyphenyl)-1H-imidazol-1-yl)-2-(methylsulfonyl) pyridine | 5-(5-(3-fluoro-4-methoxyphenyl)-1H-imidazol-1-yl)-2-(methylsulfonyl) pyridine |

TABLE 6-continued

Compounds 54-99

| Compound | Formula | Chemical name (English) | Chemical name (Chinese) |
|---|---|---|---|
| 64 | 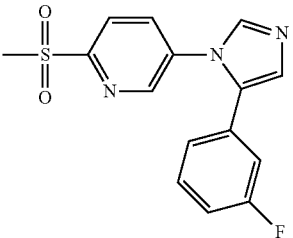 [SMILES: CS(=O)(=O)c1ccc(-n2cncc2-c2cccc(F)c2)cn1] | 5-(5-(3-fluorophenyl)-1H-imidazol-1-yl)-2-(methylsulfonyl) pyridine | 5-(5-(3-fluorophenyl)-1H-imidazol-1-yl)-2-(methylsulfonyl) pyridine |
| 65 | 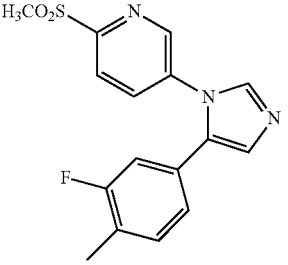 | 5-(5-(3-fluoro-4-methylphenyl)-1H-imidazol-1-yl)-2-(methylsulfonyl) pyridine | 5-(5-(3-fluoro-4-methylphenyl)-1H-imidazol-1-yl)-2-(methylsulfonyl) pyridine |
| 66 | 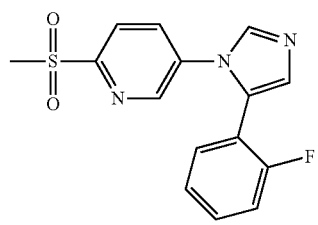 [SMILES: CS(=O)(=O)c1ccc(-n2cncc2-c2ccccc2F)cn1] | 5-(5-(2-fluorophenyl)-1H-imidazol-1-yl)-2-(methylsulfonyl) pyridine | 5-(5-(2-fluorophenyl)-1H-imidazol-1-yl)-2-(methylsulfonyl) pyridine |
| 67 | 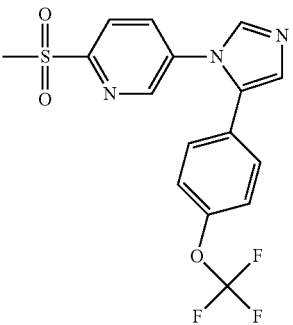 [SMILES: CS(=O)(=O)c1ccc(-n2cncc2-c2ccc(OC(F)(F)F)cc2)cn1] | 2-(methylsulfonyl)-5-(5-(4-(trifluoromethoxy)phenyl)-1H-imidazol-1-yl) pyridine | 2-(methylsulfonyl)-5-(5-(4-(trifluoromethoxy)phenyl)-1H-imidazol-1-yl) pyridine |
| 68 | 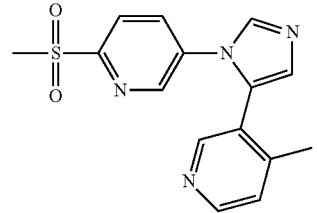 | 5-(5-(4-methylpyridin-3-yl)-1H-imidazol-1-yl)-2-(methylsulfonyl) pyridine | 5-(5-(4-methylpyridin-3-yl)-1H-imidazol-1-yl)-2-(methylsulfonyl) pyridine |

TABLE 6-continued

| | | Compounds 54-99 | |
|---|---|---|---|
| Compound | Formula | Chemical name (English) | Chemical name (Chinese) |
| 69 | | 5-(5-(2-fluoro-4-methoxyphenyl)-1H-imidazol-1-yl)-2-(methylsulfonyl) pyridine | 5-(5-(2-fluoro-4-methoxyphenyl)-1H-imidazol-1-yl)-2-(methylsulfonyl) pyridine |
| 70 | | 5-(5-(3-chloro-4-methylphenyl)-1H-imidazol-1-yl)-2-(methylsulfonyl) pyridine | 5-(5-(3-chloro-4-methylphenyl)-1H-imidazol-1-yl)-2-(methylsulfonyl) pyridine |
| 71 | | 5-(5-(3-methoxy-4-methylphenyl)-1H-imidazol-1-yl)-2-(methylsulfonyl) pyridine | 5-(5-(3-methoxy-4-methylphenyl)-1H-imidazol-1-yl)-2-(methylsulfonyl) pyridine |
| 72 | | 5-(5-(4-chlorophenyl)-1H-imidazol-1-yl)-2-(methylsulfonyl) pyridine | 5-(5-(4-chlorophenyl)-1H-imidazol-1-yl)-2-(methylsulfonyl) pyridine |
| 73 | | 5-(5-(4-chloropyridin-3-yl)-1H-imidazol-1-yl)-2-(methylsulfonyl) pyridine | 5-(5-(4-chloropyridin-3-yl)-1H-imidazol-1-yl)-2-(methylsulfonyl) pyridine |

TABLE 6-continued

Compounds 54-99

| Compound | Formula | Chemical name (English) | Chemical name (Chinese) |
|---|---|---|---|
| 74 | | 2,4-dichloro-3-(1-(6-(methylsulfonyl)pyridin-3-yl)-1H-imidazol-5-yl)pyridine | 2,4-dichloro-3-(1-(6-(methylsulfonyl)pyridin-3-yl)-1H-imidazol-5-yl)pyridine |
| 75 | | 2-chloro-4-methoxy-3-(1-(6-(methylsulfonyl)pyridin-3-yl)-1H-imidazol-5-yl) pyridine | 2-chloro-4-methoxy-3-(1-(6-(methylsulfonyl)pyridin-3-yl)-1H-imidazol-5-yl) pyridine |
| 76 | | 3,4-dichloro-5-(1-(6-(methylsulfonyl)pyridin-3-yl)-1H-imidazol-5-yl)pyridine | 3,4-dichloro-5-(1-(6-(methylsulfonyl)pyridin-3-yl)-1H-imidazol-5-yl)pyridine |
| 77 | | 2-(methylsulfonyl)-5-(5-(4-propoxyphenyl)-1H-imidazol-1-yl)pyridine | 2-(methylsulfonyl)-5-(5-(4-propoxyphenyl)-1H-imidazol-1-yl)pyridine |
| 78 | | 5-(5-(3,5-diethoxyphenyl)-1H-imidazol-1-yl)-2-(methylsulfonyl) pyridine | 5-(5-(3,5-diethoxyphenyl)-1H-imidazol-1-yl)-2-(methylsulfonyl) pyridine |

TABLE 6-continued

Compounds 54-99

| Compound | Formula | Chemical name (English) | Chemical name (Chinese) |
|---|---|---|---|
| 79 | | 5-(5-(4-ethoxyphenyl)-1H-imidazol-1-yl)-2-(methylsulfonyl) pyridine | 5-(5-(4-ethoxyphenyl)-1H-imidazol-1-yl)-2-(methylsulfonyl) pyridine |
| 80 | | 2-(methylsulfonyl)-5-(5-(4-nitrophenyl)-1H-imidazol-1-yl) pyridine | 2-(methylsulfonyl)-5-(5-(4-nitrophenyl)-1H-imidazol-1-yl) pyridine |
| 81 | | 5-(5-(4-(methylsulfinyl)phenyl)-1H-imidazol-1-yl)-2-(methylsulfonyl) pyridine | 5-(5-(4-(methylsulfinyl)phenyl)-1H-imidazol-1-yl)-2-(methylsulfonyl) pyridine |
| 82 | | 5-(5-(4-(ethylsulfinyl)phenyl)-1H-imidazol-1-yl)-2-(methylsulfonyl) pyridine | 5-(5-(4-(ethylsulfinyl)phenyl)-1H-imidazol-1-yl)-2-(methylsulfonyl) pyridine |

TABLE 6-continued

Compounds 54-99

| Compound | Formula | Chemical name (English) | Chemical name (Chinese) |
| --- | --- | --- | --- |
| 83 | | N,N-dimethyl-4-(1-(6-(methylsulfonyl) pyridin-3-yl)-1H-imidazol-5-yl) benzenamine | N,N-dimethyl-4-(1-(6-(methylsulfonyl) pyridin-3-yl)-1H-imidazol-5-yl) benzenamine |
| 84 | | 5-(5-(4-fluorophenyl)-4-methyl-1H-imidazol-1-yl)-2-(methylsulfonyl) pyridine | 5-(5-(4-fluorophenyl)-4-methyl-1H-imidazol-1-yl)-2-(methylsulfonyl) pyridine |
| 85 | | 5-(4-chloro-5-p-tolyl-1H-imidazol-1-yl)-2-(methylsulfonyl) pyridine | 5-(4-chloro-5-p-tolyl-1H-imidazol-1-yl)-2-(methylsulfonyl) pyridine |
| 86 | | 5-(4-chloro-5-(2,4-difluorophenyl)-1H-imidazol-1-yl)-2-(methylsulfonyl) pyridine | 5-(4-chloro-5-(2,4-difluorophenyl)-1H-imidazol-1-yl)-2-(methylsulfonyl) pyridine |
| 87 | | 2-chloro-3-(4-chloro-1-(6-(methylsulfonyl) pyridin-3-yl)-1H-imidazol-5-yl)-4-methoxypyridine | 2-chloro-3-(4-chloro-1-(6-(methylsulfonyl) pyridin-3-yl)-1H-imidazol-5-yl)-4-methoxypyridine |

TABLE 6-continued

Compounds 54-99

| Compound | Formula | Chemical name (English) | Chemical name (Chinese) |
|---|---|---|---|
| 88 | | 3,4-dichloro-5-(4-chloro-1-(6-(methylsulfonyl)pyridin-3-yl)-1H-imidazol-5-yl) pyridine | 3,4-dichloro-5-(4-chloro-1-(6-(methylsulfonyl)pyridin-3-yl)-1H-imidazol-5-yl) pyridine |
| 89 | | 5-(4-chloro-5-(4-propoxyphenyl)-1H-imidazol-1-yl)-2-(methylsulfonyl) pyridine | 5-(4-chloro-5-(4-propoxyphenyl)-1H-imidazol-1-yl)-2-(methylsulfonyl) pyridine |
| 90 | | 5-(4-chloro-5-(3,5-diethoxyphenyl)-1H-imidazol-1-yl)-2-(methylsulfonyl) pyridine | 5-(4-chloro-5-(3,5-diethoxyphenyl)-1H-imidazol-1-yl)-2-(methylsulfonyl) pyridine |
| 91 | | 5-(4-chloro-5-(4-ethoxyphenyl)-1H-imidazol-1-yl)-2-(methylsulfonyl) pyridine | 5-(4-chloro-5-(4-ethoxyphenyl)-1H-imidazol-1-yl)-2-(methylsulfonyl) pyridine |

TABLE 6-continued

Compounds 54-99

| Compound | Formula | Chemical name (English) | Chemical name (Chinese) |
| --- | --- | --- | --- |
| 92 | | 5-(4-chloro-5-(4-nitrophenyl)-1H-imidazol-1-yl)-2-(methylsulfonyl) pyridine | 5-(4-chloro-5-(4-nitrophenyl)-1H-imidazol-1-yl)-2-(methylsulfonyl) pyridine |
| 93 | | 5-(4-chloro-5-(4-(methylthio)phenyl)-1H-imidazol-1-yl)-2-(methylsulfonyl) pyridine | 5-(4-chloro-5-(4-(methylthio)phenyl)-1H-imidazol-1-yl)-2-(methylsulfonyl) pyridine |
| 94 | | 5-(4-chloro-5-(4-(ethylthio)phenyl)-1H-imidazol-1-yl)-2-(methylsulfonyl) pyridine | 5-(4-chloro-5-(4-(ethylthio)phenyl)-1H-imidazol-1-yl)-2-(methylsulfonyl) pyridine |
| 95 | | 3-(4-chloro-1-(6-(methylsulfonyl)pyridin-3-yl)-1H-imidazol-5-yl)-4-ethoxypyridine | 3-(4-chloro-1-(6-(methylsulfonyl)pyridin-3-yl)-1H-imidazol-5-yl)-4-ethoxypyridine |
| 96 | | 5-(4-bromo-5-(4-fluorophenyl)-1H-imidazol-1-yl)-2-(methylsulfonyl) pyridine | 5-(4-bromo-5-(4-fluorophenyl)-1H-imidazol-1-yl)-2-(methylsulfonyl) pyridine |

TABLE 6-continued

Compounds 54-99

| Compound | Formula | Chemical name (English) | Chemical name (Chinese) |
|---|---|---|---|
| 97 | | 5-(5-(4-fluorophenyl)-4-methyl-1H-imidazol-1-yl)-2-(methylsulfonyl) pyridine | 5-(5-(4-fluorophenyl)-4-methyl-1H-imidazol-1-yl)-2-(methylsulfonyl) pyridine |
| 98 | | 5-(4-chloro-5-(3,4-dichlorophenyl)-1H-imidazol-1-yl)-2-(methylsulfonyl) pyridine | 5-(4-chloro-5-(3,4-dichlorophenyl)-1H-imidazol-1-yl)-2-(methylsulfonyl) pyridine |
| 99 | | 5-(4-chloro-5-(3-chloro-4-methoxyphenyl)-1H-imidazol-1-yl)-2-(methylsulfonyl) pyridine | 5-(4-chloro-5-(3-chloro-4-methoxyphenyl)-1H-imidazol-1-yl)-2-(methylsulfonyl) pyridine |

The Activity of the Compounds of the Present Disclosure can be Detected by the Following Methods:

Human whole blood in vitro activity study: inhibition of activity of cyclooxygenase-1 (COX-1 enzyme) and cyclooxygenase-2 (COX-2 enzyme) in human blood. Whole blood were taken from healthy volunteers who had not take any non-steroidal anti-inflammatory drugs one week before, and had not drunk alcohol within 24 hours. The blood samples were divided into two parts: one was used for detecting COX-1 enzyme activity, and the other was used for detecting COX-2 enzyme activity. The compounds were dissolved in DMSO, and were prepared in advance into 2 µL solutions in respective concentrations of 500, 50, 5, 0.5, 0.05, 0.005, 0.0005 µg/mL. 200 µL whole blood without heparin was added in the tubes containing the compounds, and then incubated at 37° C. for 1 hour. The activity of COX-1 enzyme was detected by determining the amount of thromboxane B2 (TXB2) synthesized by platelet using an EIA kit. Samples tested without the compounds were negative controls. For COX-2, 200 µL whole blood with heparin was added in the tubes containing the compounds and in the tubes containing 10 µg/mL LPS. LPS control and blank control with solvent only were used respectively for determining the maximum value and the background value of the $PGE_2$ produced therefrom. The samples were incubated at 37° C. for 24 hours, and then centrifuged to collect serum/plasma, which was stored at −80° C. for detection by an EIA kit. The EIA kit of Cayman Company was used, the amounts of TXB2 and PGE2 were determined in accordance to the manufacturer's instructions, and the activities of COX-1 and COX-2 were tested respectively.

TABLE 7-1

In vitro activity assay - human whole blood test

| | $IC_{50}$ (µg/mL) | | $IC_{50}$COX-1/ |
|---|---|---|---|
| Compound No. | COX-1 | COX-2 | $IC_{50}$COX-2 |
| Compound 1 | 13.2 ± 4.45 | 0.30 ± 0.17 | 44.0 |
| Compound 1E | 25.89 ± 14.80 | 2.23 ± 1.07 | 11.6 |
| Compound 2 | 3.93 ± 1.63 | 0.18 ± 0.09 | 21.8 |
| Compound 3 | 6.86 ± 3.53 | 0.09 ± 0.03 | 76.2 |
| Compound 4 | 18.37 ± 9.54 | 0.70 ± 0.05 | 26.2 |
| Compound 5 | 0.23 ± 0.11 | 0.05 ± 0.02 | 4.6 |
| Compound 6 | 3.36 ± 1.27 | 0.13 ± 0.07 | 25.8 |
| Compound 7 | 18.07 ± 3.50 | 0.95 ± 0.34 | 19.0 |

TABLE 7-1-continued

In vitro activity assay - human whole blood test

| Compound No. | IC$_{50}$ (μg/mL) COX-1 | IC$_{50}$ (μg/mL) COX-2 | IC$_{50}$COX-1/ IC$_{50}$COX-2 |
|---|---|---|---|
| Compound 8 | >500 | 1.20 ± 0.83 | >416 |
| Compound 8E | 56.06 ± 51.30 | >500 | — |
| Compound 9 | 22.75 ± 11.25 | 0.092 ± 0.008 | 247.2 |
| Compound 10 | 70.45 ± 9.81 | 1.20 ± 0.74 | 58.8 |
| Compound 11 | >500 | 39.55 ± 9.49 | >12.6 |
| Compound 12 | 73.42 ± 20.58 | 0.54 ± 0.23 | 135.9 |
| Cimicoxib (Cimicoxib) | 1.59 ± 1.02 | 0.18 ± 0.05 | 8.8 |
| Celecoxib (Celecoxib) | 11.98 ± 6.52 | 0.78 ± 0.26 | 15.3 |

In addition, the assay results of Compound 13-Compound 99 in the in vitro testings with human whole blood indicated that, most of the IC$_{50}$ values against COX-2 were <10 μg/mL, showing a good inhibitory activity on COX-2.

In accordance with the methods described above, in vitro activity study using beagle dog whole blood was conducted, and the results were shown in Table 7-2.

TABLE 7-2

In vitro activity assay - dog whole blood test

| Compound No. | IC$_{50}$ (μg/mL) COX-1 | IC$_{50}$ (μg/mL) COX-2 | IC$_{50}$COX-1/ IC$_{50}$COX-2 |
|---|---|---|---|
| Compound 1 | 73.21 ± 32.63 | 0.88 ± 0.45 | 83.2 |
| Compound 2 | 19.67 ± 11.29 | 0.92 ± 0.55 | 21.4 |
| Compound 3 | 10.51 ± 2.72 | 0.56 ± 0.07 | 18.8 |
| Compound 9 | 201.27 ± 122.23 | 0.84 ± 0.47 | 239.6 |
| Cimicoxib (Cimicoxib) | 5.96 ± 5.29 | 0.63 ± 0.05 | 9.5 |
| Celecoxib (Celecoxib) | 8.54 ± 4.67 | 1.41 ± 1.21 | 6.1 |

In vivo test: observation of the effect of compound 1 on rat paw swelling induced by carrageenan (inflammation model evaluation)

Animal Grouping and Dosing 50 rats were randomized into 5 groups, with 10 animals in each group. Animal grouping, administration dose and volume were shown in the table below:

| Group | Dose | Volume | Animal |
|---|---|---|---|
| Model group | — | 5 | 1~10 |
| Positive control group | 14 | 5 | 11~20 |
| Low dose group (Compound | 7 | 5 | 21~30 |
| Middle dose group | 10 | 5 | 31~40 |
| High dose group (Compound | 14 | 5 | 41~50 |

Drug Preparation

The total volume prepared for each dose group was determined based on the actual weight of the animals. A corresponding volume of purified water was taken, and was added with a sample of the test compounds or of the positive control, to allow homogenous dispersion. Sodium carboxymethyl cellulose was subsequently added, to make a homogenous suspension without obvious agglomerates. The prepared concentration of each group was showed in the table below:

| Group | Drug concentration (mg/mL) | Sodium carboxymethyl cellulose (mg/mL) |
|---|---|---|
| Model group | — | 5 |
| Positive control group | 2.8 | 5 |
| Low dose group (Compound 1) | 1.5 | 5 |
| Middle dose group (Compound 1) | 2.0 | 5 |
| High dose group (Compound 1) | 2.8 | 5 |

Methods: 50 Wistar rats (3-4 weeks old, 167-199 g) were used in the study, with 25 males and 25 females. They were randomized into 5 groups, i.e. model group, positive control group, compound 1: low, middle and high dose groups. Positive control group was administered with 14 mg/kg celecoxib, low, middle and high dose groups of compound 1 were administered at a dose of 7 mg/kg, 10 mg/kg and 14 mg/kg, respectively. 1 hour after intragastric administration, 0.1 ml 1% carrageenan was intradermally injected in the right hind plantar paw to induce inflammation. After induction of inflammation, paw plantar volume and paw thickness were measured every another hour, consecutively for six times. Paw swelling rate (%) and inhibition rate (%) were calculated.

Assay methods: volume of the rat right paw was determined using UGO Basile plethysmograph, and the liquid level was kept constant for in the same animal in each measurement; thickness of the right hind paw were measured at the depiction line in the central paw with a digital vernier caliper.

The paw swelling rate (%) and inhibition rate (%) in each group of animals at each post-inflammation time points were calculated based on the following equations:

Volume swelling rate=(plantar paw volume after inflammation−plantar paw volume before inflammation)/plantar paw volume before inflammation×100%

Thickness swelling rate=(plantar paw thickness after inflammation−plantar paw thickness before inflammation)/plantar paw thickness before inflammation×100%

Inhibition rate=(average degree of swelling in model group−average degree of swelling in drug administration group)/average degree of swelling in model group×100%

The group mean and standard deviation of paw swelling rate in each group of animals were calculated, and then the following statistical analysis was performed. The test level was 0.05, and both statistical significance and biological significance were considered in the result analysis.

Levene's Test was used for homogeneity of variance test. Single-factor analysis of variance (ANOVA) was used for statistical analysis, if no statistical significance (P>0.05) was found. Dunnett's test (parametric method) analysis was used for multiple comparison analysis, if ANOVA found statistical significance (P≤0.05).

If there was heterogeneity of variance (P≤0.05), then the Kruskal-Wallis test was used. If the test result of Kruskal-Wallis test was statistically significant (P<0.05), then Dunnett's test (non-parametric method) was used for multiple comparison analysis.

Results: As shown in Tables 8-11, the results indicated that paw swelling rate was significantly decreased in positive control group compared with the model group, indicating of the animal models were successful. The low, middle and high dose groups of compound 1 all showed decreased paw swelling rate at different levels, and all showed above 30% inhibition of the paw swelling rate 4 hours after inflammation, indicating that compound 1 could significantly inhibit acute inflammation at 7 mg/kg, 10 mg/kg and 14 mg/kg dose.

TABLE 8

Observation of the effect of compound 1 on rat paw swelling induced by carrageenan - plantar paw volume swelling rate (n = 10, x̄ ± s)

| Group | Dose (mg/kg) | 1 h after inflammation | 2 h after inflammation | 3 h after inflammation | 4 h after inflammation | 5 h after inflammation | 6 h after inflammation |
|---|---|---|---|---|---|---|---|
| Model group | — | 10.90 ± 5.93 | 17.50 ± 6.33 | 21.19 ± 6.21 | 27.10 ± 7.78 | 28.04 ± 8.19 | 27.71 ± 7.72 |
| Positive control group | 14 | 10.87 ± 6.32 | 10.71 ± 6.01* | 7.16 ± 5.15* | 9.68 ± 6.13* | 12.22 ± 6.90* | 11.91 ± 5.41* |
| Compound 1 | 7 | 11.62 ± 4.73 | 12.62 ± 4.15 | 11.87 ± 3.62* | 11.14 ± 3.73* | 12.53 ± 5.03* | 11.75 ± 4.71* |
| Compound 1 | 10 | 12.48 ± 5.01 | 16.30 ± 5.55 | 15.95 ± 5.92 | 14.87 ± 5.07* | 15.48 ± 5.58* | 15.61 ± 7.62* |
| Compound 1 | 14 | 10.82 ± 4.28 | 12.15 ± 5.20 | 12.20 ± 5.19* | 13.97 ± 6.25* | 13.03 ± 4.88* | 11.10 ± 4.42* |

Note:
"*" indicating compared with the model group, $P \leq 0.05$;

TABLE 9

Observation of the effect of compound 1 on rat paw swelling induced by carrageenan - plantar paw thickness swelling rate (n = 10, x̄ ± s)

| Group | Dose (mg/kg) | 1 h after inflammation | 2 h after inflammation | 3 h after inflammation | 4 h after inflammation | 5 h after inflammation | 6 h after inflammation |
|---|---|---|---|---|---|---|---|
| Model group | — | 10.98 ± 4.18 | 15.85 ± 4.23 | 17.24 ± 4.57 | 19.03 ± 4.16 | 18.87 ± 3.88 | 15.47 ± 3.56 |
| Positive control group | 14 | 7.69 ± 3.31 | 6.30 ± 2.55* | 4.64 ± 1.99* | 3.71 ± 2.58* | 3.34 ± 2.56* | 2.72 ± 2.51* |
| Compound 1 | 7 | 7.97 ± 3.84 | 5.72 ± 4.27* | 4.01 ± 3.33* | 4.29 ± 4.47* | 2.68 ± 3.82* | 1.67 ± 4.28* |
| Compound 1 | 10 | 12.91 ± 4.89 | 7.87 ± 3.91* | 6.80 ± 3.68* | 5.78 ± 3.69* | 5.32 ± 3.99* | 5.16 ± 3.94* |
| Compound 1 | 14 | 7.25 ± 4.10 | 5.12 ± 3.74* | 3.83 ± 2.59* | 3.90 ± 3.54* | 2.55 ± 2.95* | 2.47 ± 2.70* |

Note:
"*" indicating compared with the model group, $P \leq 0.05$;

TABLE 10

Observation of the effect of compound 1 on rat paw swelling induced by carrageenan - inhibition rate of plantar paw volume swelling (n = 10, %)

| Group | Dose (mg/kg) | 1 h after inflammation | 2 h after inflammation | 3 h after inflammation | 4 h after inflammation | 5 h after inflammation | 6 h after inflammation |
|---|---|---|---|---|---|---|---|
| Positive control group | 14 | 0.26 | 38.81 | 66.24 | 64.29 | 56.44 | 57.00 |
| Low dose group (compound 1) | 7 | 0.00 | 27.91 | 43.96 | 58.90 | 55.32 | 57.59 |
| Middle dose group (compound 1) | 10 | 0.00 | 6.86 | 24.73 | 45.15 | 44.78 | 43.68 |
| High dose group (compound 1) | 14 | 0.77 | 30.59 | 42.44 | 48.46 | 53.52 | 59.93 |

TABLE 11

Observation of the effect of compound 1 on rat paw swelling induced by carrageenan - inhibition rate of plantar paw thickness swelling (n = 10, %)

| Group | Dose (mg/kg) | 1 h after inflammation | 2 h after inflammation | 3 h after inflammation | 4 h after inflammation | 5 h after inflammation | 6 h after inflammation |
|---|---|---|---|---|---|---|---|
| Positive control group | 14 | 30.02 | 60.28 | 73.09 | 80.52 | 82.31 | 82.40 |
| Low dose group (compound 1) | 7 | 27.44 | 63.92 | 76.74 | 77.45 | 85.81 | 89.21 |
| Middle dose group (compound 1) | 10 | 0.00 | 50.35 | 60.54 | 69.63 | 71.80 | 66.63 |
| High dose group (compound 1) | 14 | 33.98 | 67.67 | 77.77 | 79.53 | 86.47 | 84.04 |

In Vivo Test: Tail Suspension Test in Mice (Evaluation on an Anti-Depression Model)

Male Kunming mice, approximately 20 g, were randomized into six groups, i.e. normal group, positive drug group (fluoxetine 20 mg/kg), compound 1: group A 5 mg/kg, group B 10 mg/kg, group C 20 mg/kg, and group D 40 mg/kg.

Single Dose Test: Mice were normally fed for 1 day and allowed to adapt to the environment. Then the mice were fasted (except water) for 16 hours, and were intragastrically administrated with a single dose of the compound. The normal group was intragastrically administrated with an equivalent amount of distilled water. 40 min after the administration, the mice were inverted and fixed to a tail suspension device, and the distance between the head and the desktop was about 30 cm. Immobility time was recorded with an analysis record system, for the latter 4 min within the 6 min recording period, and was used for statistical analysis.

Study with Three-Day Consecutive Dosing: Mice were normally fed for 1 day and allowed to adapt to the environment. Then the mice were intragastrically administrated with the test drug for 3 consecutive days (once per day), and the normal group was intragastrically administrated with an equivalent amount of distilled water. The mice were fasted (except water) for 16 hours before the last dosing. 40 min after the last dosing, the mice were inverted and fixed to the tail suspension device, and the distance between the head and the desktop was about 30 cm. Immobility time was recorded with an analysis record system, for the latter 4 min within the 6 min recording period, and was used for statistical analysis.

Study with Seven-Day Consecutive Dosing: Mice were normally fed for 1 day and allowed to adapt to the environment. Then the mice were intragastrically dosed for 7 consecutive days (once/day), and the normal group was intragastrically administrated with an equivalent amount of distilled water. The mice were fasted (except water) for 16 hours before the last administration. 40 min after the last administration, the mice were inverted and fixed to the tail suspension device, and the distance between the head and the desktop was about 30 cm. Immobility time was recorded with an analysis record system, for the latter 4 min within the 6 min recording period, and was used for statistical analysis.

Results: See table 12. The results indicated that: the tail suspension immobility time was compared between the normal group and the positive groups after single dosing or after 7-day consecutive intragastric dosing, and it was found $P<0.05$; comparison was conducted between the normal group and the positive group after 3-day consecutive intragastric dosing, and it was found $P<0.01$. Both indicated significant difference, and suggested that the model was reliable. The tail suspension immobility time was compared between the normal group and the positive groups after single intragastric dosing of the test drug at 5 mg/kg, 10 mg/kg and 40 mg/kg, and it was found $P<0.05$; the immobility time was compared between the normal group and the 20 mg/kg group, and it was found $P<0.01$. Both indicated significant difference. The tail suspension immobility time was compared between the normal group and the positive groups after 3-day consecutive intragastric dosing of the test drug at 5 mg/kg and 40 mg/kg, and it was found $P<0.05$; the immobility time was compared between the normal group and the 10 mg/kg, 20 mg/kg groups, and it was found $P<0.01$. Both indicated significant difference, and showed dose dependency. The immobility time was compared between the normal group and the positive groups after 7-day consecutive intragastric dosing of the test drug at 10 mg/kg, of drug A at 20 mg/kg or 40 mg/kg, and it was found $P<0.01$. Dose dependency was also found, and it also indicated significant difference. The group dosed at 5 mg/kg showed a tendency of reduction in immobility time when compared with the normal group, but no statistical significance was found.

TABLE 12

Effect of intragastric administration of the test drug on mice tail suspension immobility time ($\overline{X} \pm S$)

| Group | Dose (mg/kg) | Single dose | | 3 days consecutive administration | | 7 days consecutive administration | |
|---|---|---|---|---|---|---|---|
| | | Animal No. | Immobility time | Animal No. | Immobility time | Animal No. | Immobility time |
| Normal group | 0 | 10 | 64.59 ± 19.26 | 11 | 60.93 ± 16.59 | 11 | 54.00 ± 19.79 |
| Positive drug group | 20 | 10 | 43.52 ± 20.21* | 10 | 33.95 ± 10.50** | 10 | 33.76 ± 10.47* |
| A | 5 | 10 | 46.57 ± 16.46* | 10 | 45.36 ± 12.09* | 10 | 45.11 ± 16.88 |
| B | 10 | 10 | 47.10 ± 17.93* | 10 | 31.94 ± 8.76** | 11 | 36.47 ± 15.13* |
| C | 20 | 10 | 43.25 ± 14.41** | 10 | 33.64 ± 15.78** | 10 | 29.98 ± 9.87** |
| D | 40 | 11 | 46.58 ± 15.32** | 10 | 41.36 ± 14.22* | 11 | 29.70 ± 15.02** |

Compared with the normal group,
*$P < 0.05$;
**$P < 0.01$

In Vivo Study: The Forced Swimming Test in Mice (Evaluation on Anti-Depression Model)

Male Kunming mice, approximately 20 g, were randomized into six groups, i.e. normal group, positive drug group (fluoxetine 20 mg/kg), group A (5 mg/kg Compound 1), group B (10 mg/kg Compound 1), group C (20 mg/kg Compound 1), and group D (40 mg/kg Compound 1).

Single Dose Test: Mice were normally fed for 1 day and allowed to adapt to the environment. Then the mice were fasted (except water) for 16 hours, and were intragastrically administrated with a single dose of the test drug, and the normal group was intragastrically administrated with an equivalent amount of distilled water. 40 min after administration, the mice were placed in forced swimming test device (swimming environment: pool diameter 12.5 cm cylinder, water temperature 25° C. and water depth 10 cm). Mice swam for six minutes, and the immobility time (i.e., the time during which the limbs were immobile, or only the feet were thrashing or paddling) was recorded with an animal behavioral record system, for the latter 4 min within the 6 min recording period, and was used for statistical analysis.

Study with Three-Day Consecutive Dosing: Mice were normally fed for 1 day and allowed to adapt to the environment. Then the mice were intragastrically administered with the test drug consecutively for three days (once per day). The normal group was intragastrically administrated equivalent amount of distilled water. Mice were fasted (except water) for 16 hours before the last dosing. 40 min after the last dosing, the mice were placed in forced swimming test device (swimming environment: pool diameter 12.5 cm cylinder, water temperature 25° C. and water depth 10 cm). Mice swam for six minutes, and the immobility time (i.e., the time during which the limbs were immobile, or only the feet were thrashing or paddling) was recorded with an animal behavioral record system, for the latter 4 min within the 6 min recording period, and was used for statistical analysis.

Study with Seven-Day Consecutive Dosing: Mice were normally fed for 1 day and allowed to adapt to the environment. Then the mice were intragastrically administered with the test drug consecutively for seven days (once per day). The normal group was intragastrically administrated equivalent amount of distilled water. Mice were fasted (except water) for 16 hours before the last dosing. 40 min after the last dosing, the mice were placed in forced swimming test device (swimming environment: pool diameter 12.5 cm cylinder, water temperature 25° C. and water depth 10 cm). Mice swam for six minutes, and the immobility time (i.e., the time during which the limbs were immobile, or only the feet were thrashing or paddling) was recorded with an animal behavioral record system, for the latter 4 min within the 6 min recording period, and was used for statistical analysis.

Results: See table 13. The forced swimming immobility time was compared between the normal group and the positive group after single intragastric dosing, and it was found $P<0.05$; comparison was conducted between the normal group and the positive groups after 3-day or 7-day consecutive intragastric dosing, and it was found $P<0.01$. Both indicated significant difference.

The forced swimming immobility time was compared between the normal group and the positive groups after single intragastric dosing of the test drug (compound 1) at 10 mg/kg, 20 mg/kg or 40 mg/kg, and significant difference was found ($P<0.01$), with dose dependency. The group dosed at 5 mg/kg showed a tendency of reduction in forced swimming immobility time when compared with the normal group, but no statistical significance was found.

The forced swimming immobility time was compared between the normal group and the positive groups after 3-day consecutive intragastric dosing of the test drug (compound 1) at 10 mg/kg, 20 mg/kg or 40 mg/kg, and significant difference was found ($P<0.01$), with dose dependency. The group dosed at 5 mg/kg showed a tendency of reduction in forced swimming immobility time when compared with the normal group, but no statistical significance was found. The forced swimming immobility time was compared between the normal group and the positive groups after 7-day consecutive intragastric dosing of the test drug (compound 1) at 10 mg/kg, 20 mg/kg or 40 mg/kg, and significant difference was found ($P<0.01$), with dose dependency. The group dosed at 5 mg/kg showed a tendency of reduction in forced swimming immobility time when compared with the normal group, but no statistical significance was found.

TABLE 13

The effect of intragastric administration of test drug on mice forced swimming immobility time ($\overline{X} \pm S$)

| Group | Dose (mg/kg) | Single dose | | 3 days consecutive administration | | 7 days consecutive administration | |
|---|---|---|---|---|---|---|---|
| | | Animal No. | Immobility time | Animal No. | Immobility time | Animal No. | Immobility time |
| Normal group | 0 | 11 | 143.37 ± 30.87 | 11 | 136.16 ± 31.42 | 10 | 130.76 ± 22.93 |
| Positive drug group | 20 | 10 | 105.04 ± 37.98* | 10 | 82.42 ± 32.07** | 10 | 90.94 ± 31.73** |
| A | 5 | 10 | 102.24 ± 27.33* | 10 | 119.73 ± 24.55 | 10 | 102.72 ± 34.07 |
| B | 10 | 11 | 92.85 ± 38.81** | 10 | 91.73 ± 22.08** | 10 | 86.40 ± 34.65** |
| C | 20 | 10 | 87.55 ± 42.50** | 11 | 83.12 ± 32.57** | 10 | 86.84 ± 30.21** |
| D | 40 | 11 | 90.86 ± 39.53** | 11 | 63.32 ± 30.46** | 11 | 83.84 ± 35.50** |

Compared with the normal group,
*$P < 0.05$;
**$P < 0.01$

Pharmacokinetic Study

Compound 1 was intravenous administrated to male SD rats in vivo [IV 2 mg/kg, 2 mg/ml, vehicle: DMSO/PEG 400/30% HP-b-CD (May 25, 1970)], $T_{1/2}$ was 5.37 h. Cimicoxib (cimicoxib) was IV administrated to male SD rats in vivo [2 mg/kg, 2 mg/ml, menstruum: DMSO/PEG 400/30% HP-b-CD (May 25, 1970)], $T_{1/2}$ was 3.20 h. The half-life of compound 1 was longer than cimicoxib. Pharmacokinetic parameters of the both were shown in the table below:

| Pharmacokinetic parameters | Compound 1 | Cimicoxib |
|---|---|---|
| $t_{1/2}$ (hr) | 5.37 ± 0.51 | 3.20 ± 0.80 |
| $C_0$ (ng/mL) | 1703 ± 259 | 1977 ± 140 |
| $AUC_{last}$ (hr * ng/mL) | 11371 ± 949 | 11990 ± 4401 |
| Vss (L/kg) | 1.16 ± 0.02 | 0.773 ± 0.145 |
| CL (mL/min/kg) | 2.83 ± 0.27 | 2.99 ± 0.92 |

What is claimed is:

1. A compound of formula (I), or its pharmaceutically acceptable salt, solvate, or isomer, wherein the isomer is a stereoisomer or a geometric isomer,

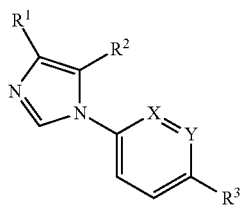

(I)

wherein:
when X=N, Y=C or Y=N, X=C atom;
substituent group $R^1$ represents halogen;
substituent group $R^2$ represents aryl or heteroaryl substituted independently by one or more groups which are selected from a group consisting of halogen, hydrogen, $C_{1-8}$ alkyl, or $R^4OC_{0-8}$ alkyl;
substituent group $R^3$ represents $SO_2R^7$;
substituent group $R^4$ represents $C_{1-8}$ alkyl; and
substituent group $R^7$ represents $C_{1-8}$ alkyl.

2. The compound of claim 1, or its pharmaceutically acceptable salt, solvate, or isomer, wherein:
when X=N, Y=C or Y=N, X=C atom,
the substituent group $R^1$ represents halogen;
the substituent group $R^2$ represents aryl or heteroaryl independently substituted by one or more groups which are selected from a group consisting of halogen, hydrogen, $C_{1-5}$ alkyl, or $R^4OC_{0-5}$ alkyl;
the substituent group $R^4$ represents $C_{1-5}$ alkyl; and
the substituent group $R^7$ represents $C_{1-5}$ alkyl.

3. The compound of claim 2, or its pharmaceutically acceptable salt, solvate, or isomer, wherein:
the substituent group $R^2$ represents aryl or heteroaryl substituted independently by one or more groups which are selected from a group consisting of halogen, hydrogen, $C_{1-4}$ alkyl, or $R^4OC_{0-4}$ alkyl;
the substituent group $R^4$ represents $C_{1-4}$ alkyl; and
the substituent group $R^7$ represents $C_{1-4}$ alkyl.

4. The compound of claim 3, or its pharmaceutically acceptable salt, solvate, or isomer, wherein:
the substituent group $R^1$ represents chlorine atom, or bromine atom;
the substituent group $R^2$ represents aryl or heteroaryl substituted independently by one or more groups which are selected from a group consisting of halogen, hydrogen, $C_{1-3}$ alkyl, or $R^4OC_{0-4}$ alkyl; and
the substituent group $R^4$ represents $C_{1-4}$ alkyl.

5. The compound of claim 4, or its pharmaceutically acceptable salt, solvate, or isomer, wherein:
the substituent group $R^1$ represents chlorine atom;
the substituent group $R^2$ represents aryl or heteroaryl substituted independently by one or more groups which are selected from a group consisting of halogen, hydrogen, $C_{1-3}$ alkyl, $C_{1-3}$ alkoxy; and
the substituent group $R^7$ represents methyl.

6. The compound of claim 5, or its pharmaceutically acceptable salt, solvate, or isomer, wherein the compound is selected from:
2-(4-chloro-5-phenyl-1H-imidazol-1-yl)-5-(methylsulfonyl) pyridine,
2-(4-chloro-5-(4-fluorophenyl)-1H-imidazol-1-yl)-5-(methylsulfonyl) pyridine,
2-(4-chloro-5-p-tolyl-1H-imidazol-1-yl)-5-(methylsulfonyl) pyridine,
2-(4-chloro-5-(2,4-dichlorophenyl)-1H-imidazol-1-yl)-5-(methylsulfonyl) pyridine,
2-(4-chloro-5-(3-fluoro-4-methoxyphenyl)-1H-imidazol-1-yl)-5-(methylsulfonyl) pyridine,
5-(4-chloro-5-phenyl-1H-imidazol-1-yl)-2-(methylsulfonyl) pyridine,
5-(4-chloro-5-(4-methoxyphenyl)-1H-imidazol-1-yl)-2-(methylsulfonyl) pyridine,
5-(4-chloro-5-(3-fluoro-4-methoxyphenyl)-1H-imidazol-1-yl)-2-(methylsulfonyl) pyridine, and
5-(4-chloro-5-(4-fluorophenyl)-1H-imidazol-1-yl)-2-(methylsulfonyl) pyridine.

7. The compound of claim 1, or its pharmaceutically acceptable salt, solvate, or isomer, wherein the compound is selected from:
2-(4-chloro-5-phenyl-1H-imidazol-1-yl)-5-(methylsulfonyl) pyridine,
2-(4-chloro-5-p-tolyl-1H-imidazol-1-yl)-5-(methylsulfonyl) pyridine,
2-(4-chloro-5-(2,4-dichlorophenyl)-1H-imidazol-1-yl)-5-(methylsulfonyl) pyridine,
2-(4-chloro-5-(3-fluoro-4-methoxyphenyl)-1H-imidazol-1-yl)-5-(methylsulfonyl) pyridine,
5-(4-chloro-5-phenyl-1H-imidazol-1-yl)-2-(methylsulfonyl) pyridine,
5-(4-chloro-5-(4-methoxyphenyl)-1H-imidazol-1-yl)-2-(methylsulfonyl) pyridine,
5-(4-chloro-5-(3-fluoro-4-methoxyphenyl)-1H-imidazol-1-yl)-2-(methylsulfonyl) pyridine, and
5-(4-chloro-5-(4-fluorophenyl)-1H-imidazol-1-yl)-2-(methylsulfonyl) pyridine.

8. The compound of claim 1, or its pharmaceutically acceptable salt, solvate, or isomer, wherein the compound is selected from:
2-(4-chloro-5-phenyl-1H-imidazol-1-yl)-5-(methylsulfonyl) pyridine,
2-(4-chloro-5-p-tolyl-1H-imidazol-1-yl)-5-(methylsulfonyl) pyridine,
5-(4-chloro-5-phenyl-1H-imidazol-1-yl)-2-(methylsulfonyl) pyridine,
5-(4-chloro-5-(4-methoxyphenyl)-1H-imidazol-1-yl)-2-(methylsulfonyl) pyridine,
5-(4-chloro-5-(3-fluoro-4-methoxyphenyl)-1H-imidazol-1-yl)-2-(methylsulfonyl) pyridine, and
5-(4-chloro-5-(4-fluorophenyl)-1H-imidazol-1-yl)-2-(methylsulfonyl) pyridine.

9. A preparation process of a compound of formula (I) of claim 1, or its pharmaceutically acceptable salt, solvate, or isomer, wherein the preparation process comprises the following steps:

a) reacting an imine of formula II with an isocyanide of formula III to obtain a compound of formula (IV), wherein X, Y, R², and R⁷ in the formula (II) are defined as in claim 1, wherein L in the formula (III) represents a leaving group;

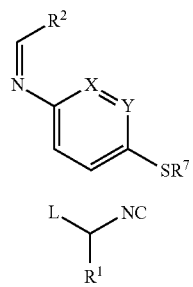

b) oxidizing a sulfide of formula (IV) to convert it to a compound of formula (V),

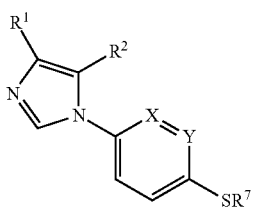

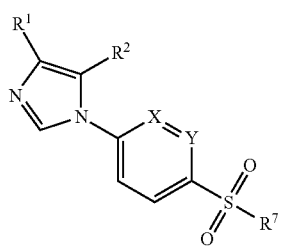

wherein R², R⁷, X and Y are defined as in claim 1; and c) reacting the compound of formula (V) with a halogenated reagent to allow conversion to a compound of formula (VI)

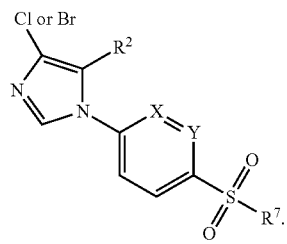

10. A pharmaceutical composition, comprising an effective amount of a compound of claim 1, or its pharmaceutically acceptable salt, solvate, or isomer, and one or more pharmaceutically acceptable excipients.

11. The pharmaceutical composition of claim 10, which is the form of a tablet, a capsule or injection.

12. The compound of claim 1, or its pharmaceutically acceptable salt, solvate, or isomer, wherein the compound is selected from:

2-(4-chloro-5-phenyl-1H-imidazol-1-yl)-5-(methylsulfonyl) pyridine, 2-(4-chloro-5-p-tolyl-1H-imidazol-1-yl)-5-(methylsulfonyl) pyridine, 5-(4-chloro-5-phenyl-1H-imidazol-1-yl)-2-(methylsulfonyl) pyridine, 5-(4-chloro-5-(4-methoxyphenyl)-1H-imidazol-1-yl)-2-(methylsulfonyl) pyridine, and 5-(4-chloro-5-(4-fluorophenyl)-1H-imidazol-1-yl)-2-(methylsulfonyl) pyridine.

13. The compound of claim 1, or its pharmaceutically acceptable salt, solvate, or isomer, wherein the compound is selected from:

5-(4-chloro-5-phenyl-1H-imidazol-1-yl)-2-(methylsulfonyl) pyridine, 5-(4-chloro-5-(4-methoxyphenyl)-1H-imidazol-1-yl)-2-(methylsulfonyl) pyridine, and 5-(4-chloro-5-(4-fluorophenyl)-1H-imidazol-1-yl)-2-(methylsulfonyl) pyridine.

14. The compound of claim 1, or its pharmaceutically acceptable salt, solvate, or isomer, wherein the compound is selected from:

5-(4-chloro-5-phenyl-1H-imidazol-1-yl)-2-(methylsulfonyl) pyridine and 5-(4-chloro-5-(4-methoxyphenyl)-1H-imidazol-1-yl)-2-(methylsulfonyl) pyridine.

* * * * *